US008168327B2

(12) United States Patent
Morishita et al.

(10) Patent No.: US 8,168,327 B2
(45) Date of Patent: May 1, 2012

(54) IMIDE DERIVATIVE, MATERIAL FOR ORGANIC ELECTROLUMINESCENT DEVICE AND ORGANIC ELECTROLUMINESCENT DEVICE USING THE SAME

(75) Inventors: Hironobu Morishita, Sodegaura (JP); Hisayuki Kawamura, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1341 days.

(21) Appl. No.: 11/619,787

(22) Filed: Jan. 4, 2007

(65) Prior Publication Data
US 2007/0160905 A1 Jul. 12, 2007

(30) Foreign Application Priority Data

Jan. 11, 2006 (JP) ................................. 2006-003714
Mar. 30, 2006 (JP) ................................. 2006-094411

(51) Int. Cl.
*B32B 27/00* (2006.01)
(52) U.S. Cl. ............... 429/212; 428/473.5; 429/213; 548/100; 548/152; 548/156; 548/160; 548/219
(58) Field of Classification Search .............. 564/429, 564/428, 426; 428/473.5; 429/212, 213, 429/473.5; 548/156, 100, 152, 160, 219
See application file for complete search history.

(56) References Cited

U.S. PATENT DOCUMENTS

| 4,468,444 | A | 8/1984 | Contois |
| 4,720,432 | A | 1/1988 | VanSlyke et al. |
| 5,061,569 | A | 10/1991 | VanSlyke et al. |
| 5,639,914 | A | 6/1997 | Tomiyama et al. |
| 6,646,164 | B2 * | 11/2003 | Uemura et al. ............ 564/429 |
| 2002/0128514 | A1 | 9/2002 | Uemura et al. |

FOREIGN PATENT DOCUMENTS

| CA | 2 277 644 A1 | 1/2000 |
| EP | 0 650 955 A1 | 5/1995 |
| EP | 0 973 210 A2 | 1/2000 |
| JP | 61-78890 | 4/1986 |
| JP | 2-15084 | 1/1990 |
| JP | 2-189524 | 7/1990 |
| JP | 4-297076 | 10/1992 |
| JP | 7-126226 | 5/1995 |
| JP | 2704200 B2 | 1/1998 |
| JP | 11-251067 | 9/1999 |
| JP | 2000-86595 | 3/2000 |
| JP | 2000-196140 | 7/2000 |
| JP | 2001-40237 | 2/2001 |
| JP | 2001-114735 | 4/2001 |
| JP | 2001-297883 | 10/2001 |
| JP | 2003-31365 | 1/2003 |
| JP | 2004-514257 | 5/2004 |
| JP | 2005-208617 | 8/2005 |
| WO | WO 02/41414 A1 | 5/2002 |

OTHER PUBLICATIONS

Matsuura et al (Polyimides derived from 2,2'-bis(trifluoromethyl)-4,4'-diaminobiphenyl. 2. Synthesis and characterization of polyimides prepared from fluorinated benzenetetracarboxylic dianhydrides, Macromolecules, vol. 25, pp. 3540-3545, 1992).*
Kazuhiko Seki, et al., "Energy level alignment at organic/metal interfaces studied by UV photoemission", Synthetic Metals, vol. 91, Nos. 1-3, Dec. 1997, cover page and pp. 137-142, Dec. 16, 2011.
Duygu Uzun, et al., "Synthesis and photophysical properties of N,N'-bis(4-cyanophenyl)-3,4,9,10-perylenebis(dicarboximide) and N,N'-bis(4-cyanophenyl)-1,4,5,8-naphthalenediimide", Journal of Photochemistry and Photobiology A: Chemistry, vol. 156, Nos. 1-3, Mar. 20, 2003, cover page and pp. 45-54.
C. W. Tang, et al., "Organic electroluminescent diodes", Applied Physics Letters, vol. 51, No. 12, Sep. 21, 1987, cover page and pp. 913-915.
Japan Polyimide Forum, Latest Polyimide, NTS inc. and the like, pp. 90-99, 140-145 and 178-187.
K Books Series 122, May 1, 1997, cover page, pp. 224-229 and end page.

* cited by examiner

*Primary Examiner* — Gregory Listvoyb
(74) *Attorney, Agent, or Firm* — Oblon, Spivak, McClelland, Maier & Neustadt, L.L.P.

(57) ABSTRACT

An imide derivative represented by the following formula (A):

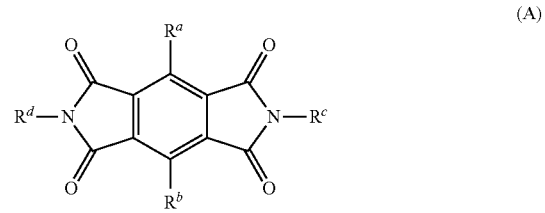

wherein $R^a$ and $R^b$ are each a hydrogen atom, a halogen atom, a cyano group, an alkyl group, a fluoroalkyl group or an aryl group; at least one of $R^a$ and $R^b$ is a fluoroalkyl group; and $R^c$ and $R^d$ are each a substituted or unsubstituted benzyl group, an aryl group, a heterocycle, a fluoroalkyl group or an imide group.

9 Claims, 1 Drawing Sheet

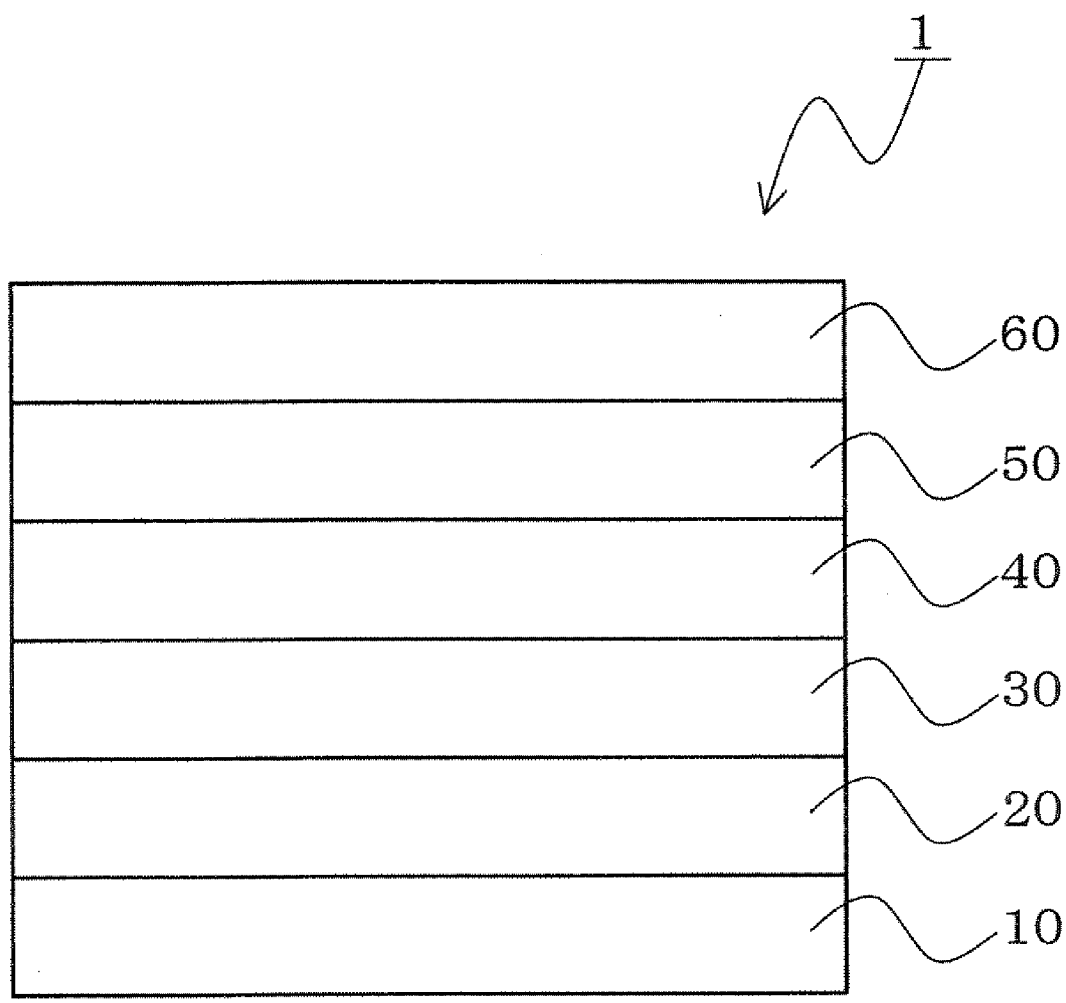

IMIDE DERIVATIVE, MATERIAL FOR ORGANIC ELECTROLUMINESCENT DEVICE AND ORGANIC ELECTROLUMINESCENT DEVICE USING THE SAME

TECHNICAL FIELD

The invention relates to a novel imide derivative, a material for an organic electroluminescent device and an organic electroluminescent device using the same.

BACKGROUND

An organic electroluminescent device (hereinafter, "electroluminescent" is often abbreviated as "EL") is a self-emission device utilizing the principle that a fluorescent material emits light by the recombination energy of holes injected from an anode and electrons injected from a cathode when an electric field is applied.

Since C. W. Tang et al. of Eastman Kodak Co. reported a low-voltage driven organic EL device of stacked type (non-Patent Document 1, for example), studies on organic EL devices in which organic materials are used as constitution materials has been actively made.

The organic EL device reported by Tang et al. has a stacked structure in which tris(8-hydroxyquinolinol)aluminum is used as an emitting layer and a triphenyldiamine derivative is used as a hole transporting layer. The advantage of the stacked structure include increased injection efficiency of holes to the emitting layer, increased generation efficiency of excitons generated by recombination while blocking electrons injected from the cathode, and containing the excitons generated in the emitting layer.

As the stacking structure of the organic EL device, a two-layer type formed of a hole transporting (injecting) layer and an electron-transmitting layer, or a three-layer type formed of a hole transporting (injecting) layer, an emitting layer, and an electron transporting (injecting) layer or the like is well known. In such a device with a stacked structure, the device structures or the fabrication methods have been contrived to increase recombination efficiency of injected holes and electrons.

Heretofore, an aromatic diamine derivative as described in Patent Document 1 or an aromatic condensed ring diamine derivative as described in Patent Document 2 is known as a hole transporting material used in an organic EL device.

In an organic EL device using the aromatic diamine derivative as the hole transporting material, a high applied voltage is required in order to obtain a sufficient luminance. Applying a high voltage causes such problems as shortened lifetime of the device, increased power consumption, and the like.

To solve the problems, doping a hole-injection layer with an electron-receiving compound such as Lewis acid or the like has been proposed (Patent Documents 3 to 6, or the like) However, the electron-receiving compounds used in those Patent Documents have disadvantages that they are unstable to handle during fabricating an organic EL device, that the lifetime of an organic EL device fabricated using these compounds is shortened due to a lowering in stability such as heat resistance when an organic EL device is driven, and the like.

Tetrafluorodicyanoquinodimethane of an electron-receiving compound described in Patent Documents 5, 7, 8 and the like is sublimed readily since it has a low molecular weight and is substituted with fluorine. Therefore, tetrafluorodicyanoquinodimethane may diffuse within an apparatus when fabricating an organic EL device by vacuum deposition, causing the apparatus or the device to be contaminated. In addition, it is crystallized when forming a device therefrom to cause current leakage.

The inventors focused attention on an imide derivative and made extensive studies. In more detail, the inventors focused attention on naphthalene tetracarboxylic acid diimide derivatives and pyromellitic acid diimide derivatives. It is known that these compounds form charge transfer complexes with amine derivatives of donor compounds (Non-patent Document 2). These compounds are also known as a material for an electrophotographic photoreceptor (Patent Document 9).

Since the above-mentioned imide derivatives have electron receiving properties and excel in heat resistance, it is expected that the productivity is not decreased due to decomposition thereof during depositing, and the resulting EL device does not deteriorate due to Joule heat and the like which occurs during driving of the device.

However, a reduction potential of the imide derivatives, which are used for an electron transporting material of an electrophotographic photoreceptor, is $-1.5$ to $-0.5$ V (vs saturated calomel electrode, and "vs saturated calomel electrode" is often abbreviated as "vs SCE" hereinafter), and the electron receiving properties thereof are weak. Therefore, the imide derivatives have an insufficient performance so that they cannot be used for an organic EL device.

[Patent Document 1] U.S. Pat. No. 4,720,432
[Patent Document 2] U.S. Pat. No. 5,061,569
[Patent Document 3] JP-A-2003-031365
[Patent Document 4] JP-A-2001-297883
[Patent Document 5] JP-A-2000-196140
[Patent Document 6] JP-A-11-251067
[Patent Document 7] JP-A-4-297076
[Patent Document 8] JP-T-2004-514257
[Patent Document 9] JP-A-2001-040237
[Non-patent document 1] C. W. Tang, S. A. Vanslyke, Applied Physics Letters, 51, 913 (1987)
[Non-patent document 2] Japan Polyimide Forum, Latest Polyimide, NTS inc. and the like The invention has been made based on the above problems. An object of the invention is to provide an electron-receiving material suitable as a constitution material of an organic EL device.

An object of the invention is to provide an organic EL device which can be driven at a low voltage and have a long lifetime.

The inventors made extensive studies and found that a novel imide compound or a specific imide derivative, which is derived from a pyromellitic acid of electron-receiving compound and has an electron-withdrawing group, has high electron-receiving properties, and improved heat resistance and electrical characteristics. The inventors found that an organic EL device using this imide derivative as an organic EL device material can be driven at a low voltage and can exhibit a long lifetime.

The invention provides the following imide derivative, and the like.

1. An imide derivative represented by the following formula (A):

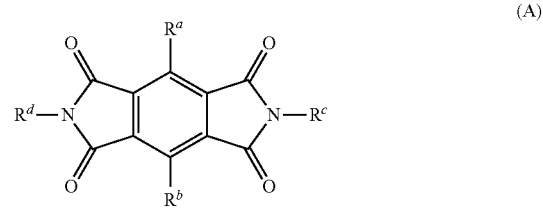

wherein $R^a$ and $R^b$ are each a hydrogen atom, a halogen atom, a cyano group, an alkyl group, a fluoroalkyl group or an aryl group; at least one of $R^a$ and $R^b$ is a fluoroalkyl group; and $R^c$ and $R^d$ are each a substituted or unsubstituted benzyl group, an aryl group, a heterocycle, a fluoroalkyl group or an imide group.

2. A material for an organic electroluminescent device represented by the following formula (I):

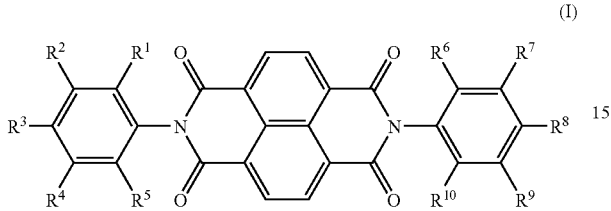

wherein $R^1$ to $R^{10}$ are each a hydrogen atom, a halogen atom, a fluoroalkyl group or a cyano group, provided that a material wherein all of $R^1$ to $R^{10}$ are a hydrogen atom is excluded.

3. A material for an organic electroluminescent device represented by the following formula (II):

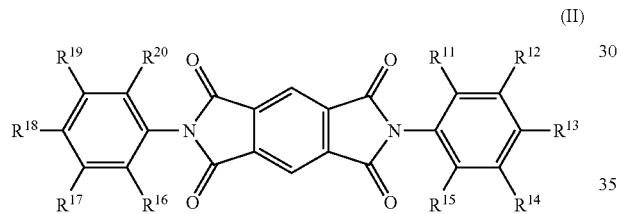

wherein $R^{11}$ to $R^{20}$ are each a hydrogen atom, a halogen atom, a fluoroalkyl group or a cyano group, provided that a material wherein all of $R^{11}$ to R20 are a hydrogen atom is excluded.

4. The material for an organic electroluminescent device according to any one of 1 to 3 which have a reduction potential (vs saturated calomel electrode) in a dimethylformamide solution of −0.5 V or more.

5. An organic electroluminescent device comprising:
   an anode,
   a cathode, and
   one or a plurality of organic thin layers, including an emitting layer, the organic thin layers being interposed between the anode and the cathode;
   at least one of the organic thin layers containing the imide derivative of claim 1 or the material for an organic electroluminescent device of any one of 1 to 4.

6. The organic electroluminescent device according to 5 wherein the organic thin layers are a multilayer body in which a hole transporting layer, an emitting layer and an electron transporting layer are stacked in this order from the anode.

7. The organic electroluminescent device according to 6 wherein the hole transporting layer contains the imide derivative or the material for an organic electroluminescent device.

8. The organic electroluminescent device according to 5 wherein the organic thin layers are a multilayer body in which a hole injecting layer, a hole transporting layer, an emitting layer, and an electron transporting layer are stacked in this order from the anode; the hole injection layer containing the imide derivative or the material for an organic electroluminescent device.

9. The organic electroluminescent device according to 7 or 8 wherein the hole transporting layer or the hole injecting layer, the hole transporting layer and the hole injecting layer containing the imide derivative or the material for an organic electroluminescent device, further contains a phenylenediamine compound represented by the following formula (III):

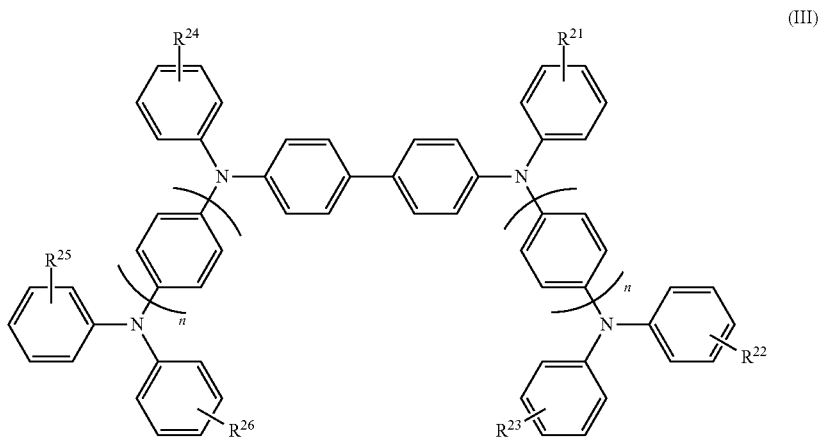

wherein $R^{21}$ to $R^{26}$ are a hydrogen atom, a halogen atom, a trifluoromethyl group, an alkyl group, an aryl group, or a heterocycle; $R^{21}$ to $R^{26}$ may form a naphthalene skeleton, a carbazole skeleton, or a fluorene skeleton with a phenyl group bonded; and n represents 1 or 2.

According to the invention, a novel material for an organic EL device is provided. Also, according to the invention, an organic EL device which can be driven at a low voltage and has a long lifetime is provided.

BRIEF DESCRIPTION OF THE DRAWINGS

FIG. 1 is a systematic cross-sectional view showing one embodiment of the organic EL device of the invention.

DETAILED DESCRIPTION OF THE PREFERRED EMBODIMENTS

Firstly, the imide derivative of the invention will be described.

The imide derivative is a compound represented by the following formula (A):

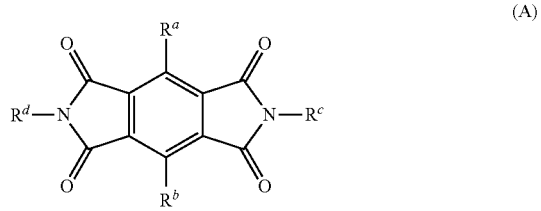

(A)

wherein $R^a$ and $R^b$ are each a hydrogen atom, a halogen atom, a cyano group, an alkyl group, a fluoroalkyl group or an aryl group; at least one of $R^a$ and $R^b$ is a fluoroalkyl group; and $R^c$ and $R^d$ are each a substituted or unsubstituted benzyl group, an aryl group, a heterocycle, a fluoroalkyl group or an imide group.

The imide derivative represented by the formula (A) has electron-receiving properties. Therefore, when using in an organic EL device, the organic EL device can be driven at a low voltage and can exhibit a prolonged lifetime.

In addition, since the compound does not scatter within a film-forming apparatus during manufacturing an organic EL device, the film-forming apparatus or the organic EL device is not contaminated.

In the formula (A), the halogen atom represented by $R^a$ and $R^b$ is preferably fluorine or chlorine.

The alkyl group represented by $R^a$ and $R^b$ is preferably a methyl group, an isopropyl group or a tert-butyl group.

The fluoroalkyl group represented by $R^a$ and $R^b$ is preferably a trifluoromethyl group or a pentafluoroethyl group.

The aryl group represented by $R^a$ and $R^b$ is preferably a phenyl group or a naphthyl group.

In the formula (A), the substituent of the benzyl group represented by $R^c$ and $R^d$ is preferably a fluoro group, a trifluoromethyl group or a cyano group.

The aryl group represented by $R^c$ and $R^d$ is preferably a substituted or unsubstituted phenyl group or a naphthyl group.

As the substituents, a fluoro group, a fluoroalkyl group, cyano group and the like can be given.

The heterocycle represented by $R^c$ and $R^d$ is preferably a pyridine ring or a pyrazine ring.

The fluoroalkyl group represented by $R^c$ and $R^d$ is preferably a perfluorobutyl group or perfluorohexyl group.

The imide group represented by $R^c$ and $R^d$ is preferably substituents shown below.

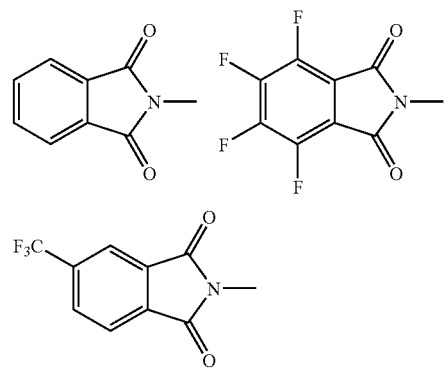

For example, the imide derivative of the invention can be synthesized by reacting a tetracarboxylic anhydride, which is synthesized by the method (the scheme shown by the following) described in the document (Macromolecules, 25, 3540, 1992), with an amine compound.

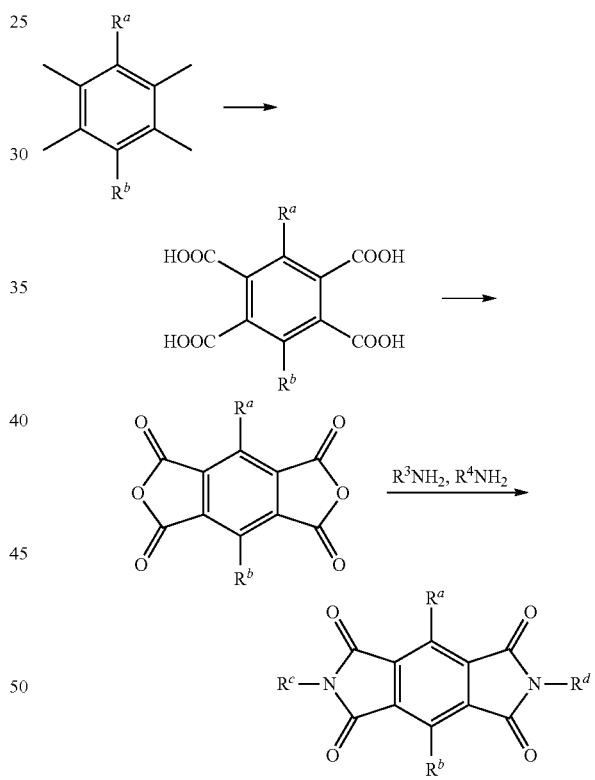

The imide derivative of the invention preferably has a reduction potential (vs SCE) in a dimethylformamide (DMF) solution of −0.5 V or more.

The electron-receiving properties can be further increased by using a compound with a reduction potential of −0.5V or more. The reduction potential is particularly preferably −0.4 V or more.

Preferred examples of the compounds represented by the formula (A) are given below. Examples of a method of synthesizing the compounds will be described in detail in the examples given later.

(A-1) 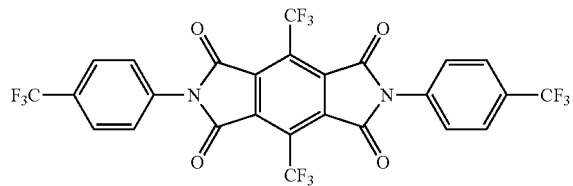
(A-2) 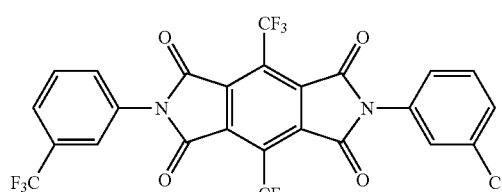
(A-3) 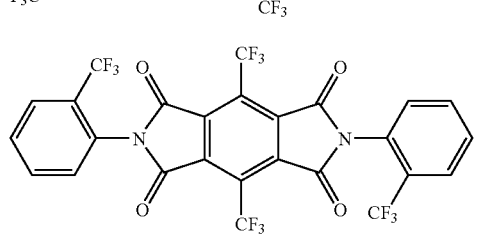
(A-4) 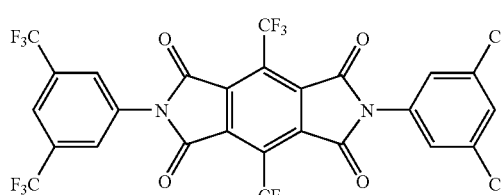
(A-5) 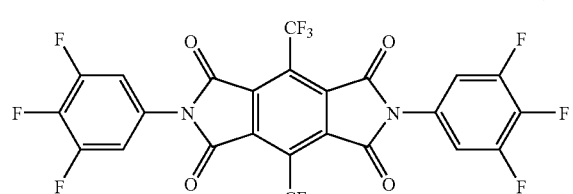
(A-6) 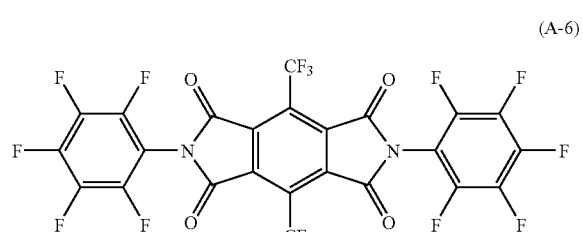
(A-7) 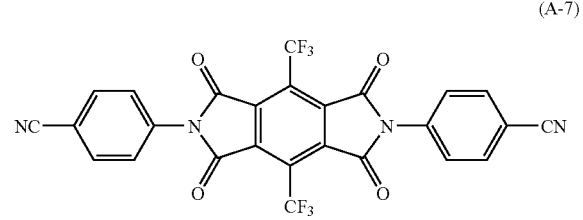
(A-8) 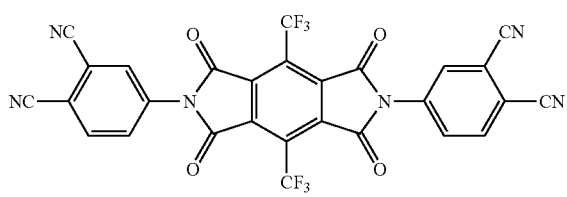
(A-9) 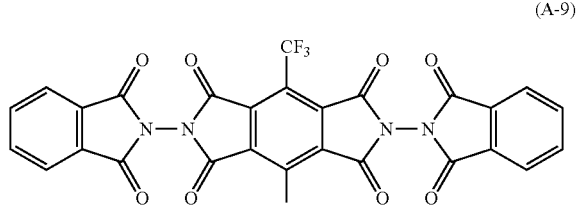
(A-10) 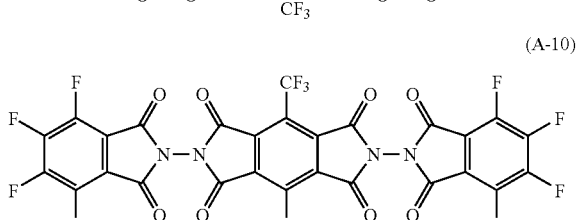
(A-11) 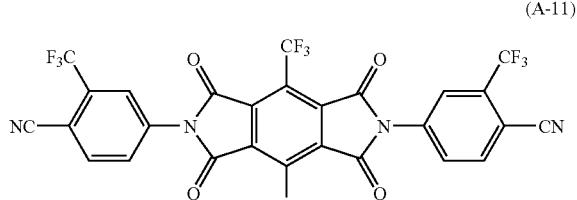
(A-12) 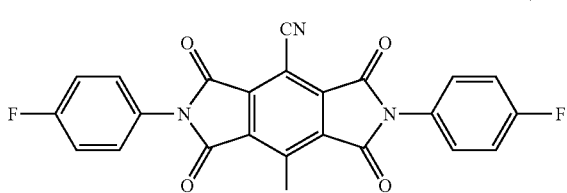
(A-13) 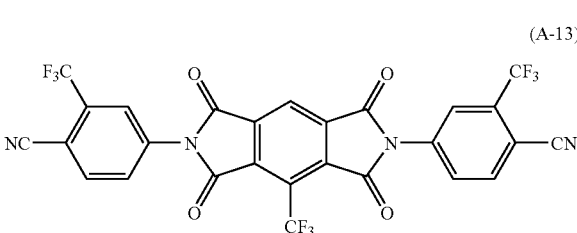
(A-14) 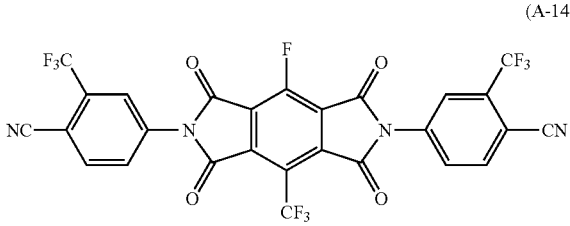

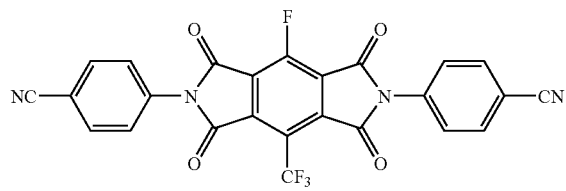
(A-15)

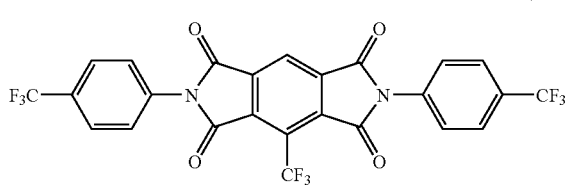
(A-16)

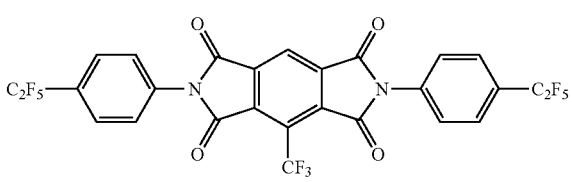
(A-17)

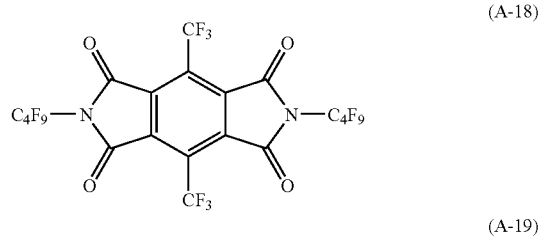
(A-18)

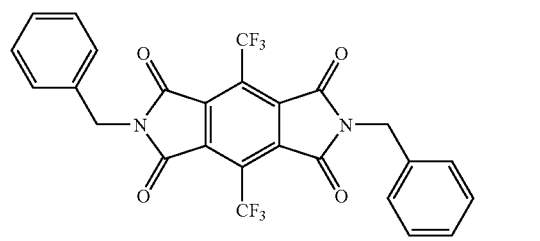
(A-19)

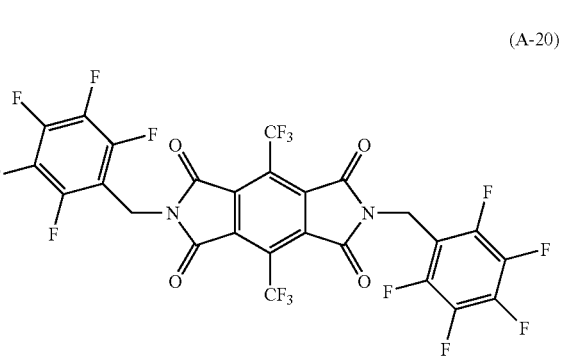
(A-20)

Next, the material for an organic EL device of the invention will be described.

The material for an organic EL device is a naphthalenetetracarboxylic diimide derivative represented by the following formula (I) or a pyromellitic diimide derivative represented by the following formula (II).

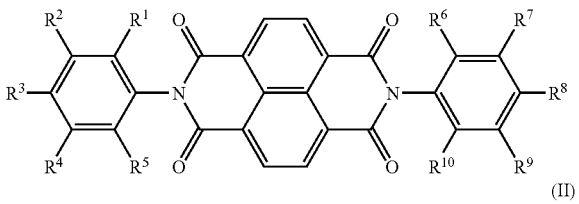
(I)

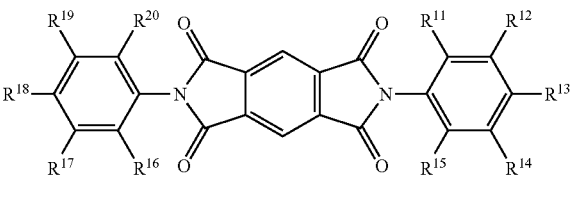
(II)

In the formula (I), $R^1$ to $R^{10}$ are each a hydrogen atom, a halogen atom, a fluoroalkyl group or a cyano group, provided that a material wherein all of $R^1$ to $R^{10}$ are a hydrogen atom is excluded.

In the formula (II), $R^{11}$ to $R^{20}$ are each a hydrogen atom, a halogen atom, a fluoroalkyl group or a cyano group, provided that a material wherein all of $R^{11}$ to $R^{20}$ are a hydrogen atom is excluded.

The imide derivative represented by the formula (I) or (II) has electron-receiving properties. Therefore, when using in an organic EL device, the organic EL device can be driven at a low voltage and can exhibit a prolonged lifetime.

In addition, since the compound does not scatter within a film-forming apparatus during manufacturing an organic EL device, the film-forming apparatus or the organic EL device is not contaminated.

In the formulas (I) and (II), the halogen atom represented by $R^{11}$ to $R^{20}$ is preferably fluorine or chlorine, for example.

In the formulas (I) and (II), as examples of the fluoroalkyl group represented by $R^1$ to $R^{20}$, a trifluoromethyl group, a pentafluoroethyl group, a perfluorocyclohexyl group, a perfluoroadamantyl group and the like can be given. Of these, a trifluoromethyl group is preferable.

The material for an organic EL device of the invention preferably has a reduction potential (vs SCE) in a dimethylformamide (DMF) solution of −0.5 V or more.

The electron-receiving properties can be further increased by using a compound with a reduction potential of −0.5V or more. The reduction potential is particularly preferably −0.4 V or more.

Examples of an imide derivative preferably used as the material for an organic EL device of the invention are given below. Examples of a method of synthesizing the compounds will be described in detail in the examples given later.

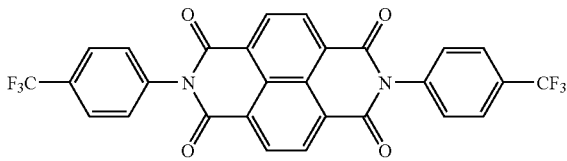
(I-1)

-continued
(I-2)
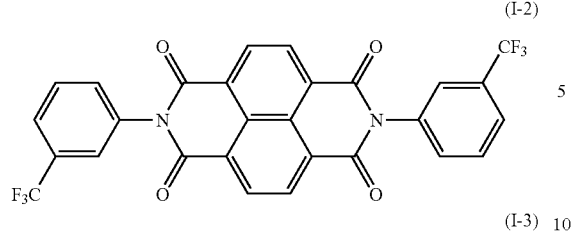
(I-3)
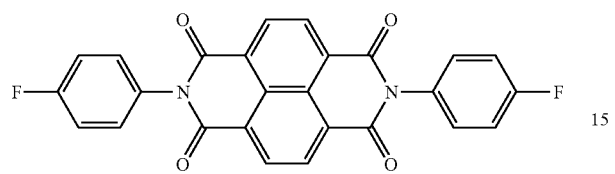
(I-4)
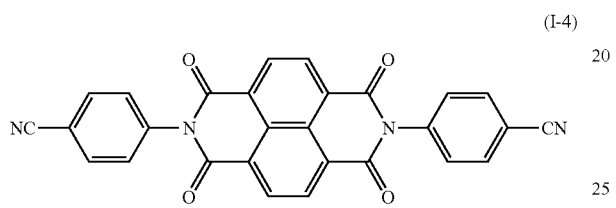
(I-5)
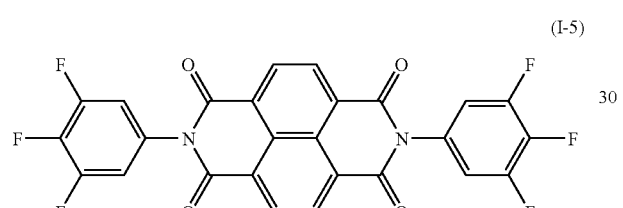
(I-6)
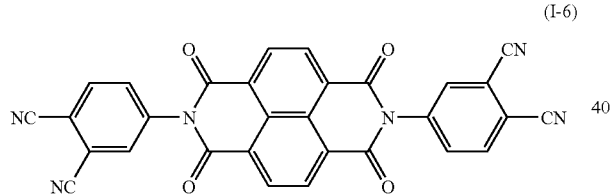
(I-7)
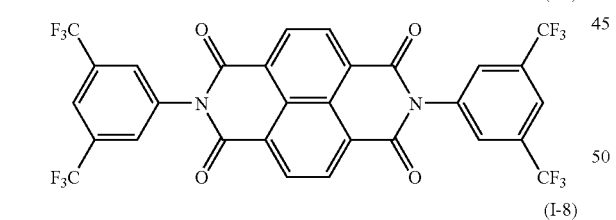
(I-8)
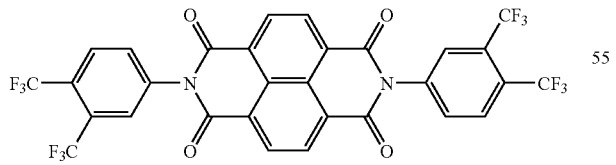
(II-1)
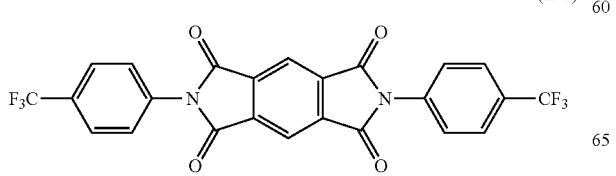
-continued
(II-2)
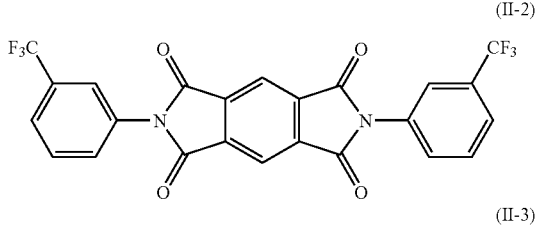
(II-3)
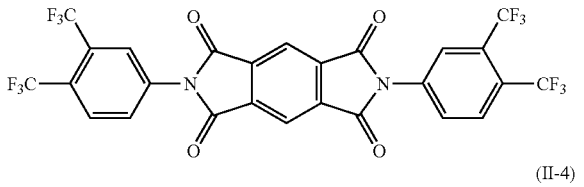
(II-4)
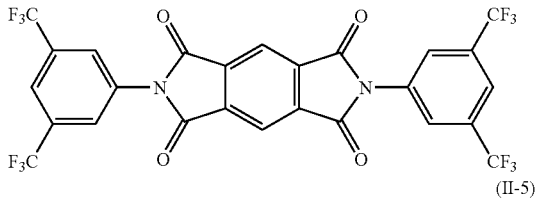
(II-5)
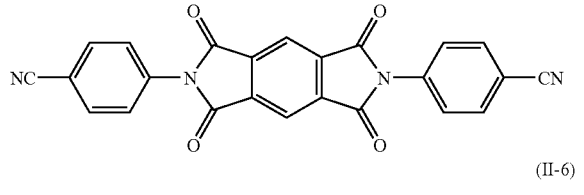
(II-6)
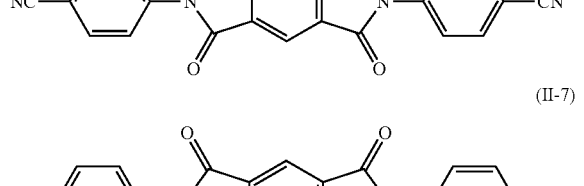
(II-7)
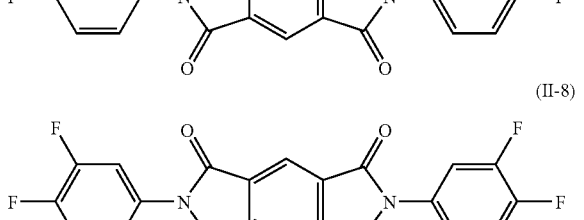
(II-8)
(II-9)
Next, the organic EL device of the invention will be described.
The organic EL device of the invention has one or a plurality of organic thin layers, the organic thin layers including an emitting layer, interposed between an anode and a cathode. At least one of the organic thin layers contains the imide derivative of the invention or the material for an organic EL device of the invention (hereinafter, "both the derivative and the material" is referred to as "material for an organic EL device").

FIG. 1 is a systematic cross-sectional view showing one embodiment of the organic EL device of the invention.

In the organic EL device 1, an anode 10, a hole injecting layer 20, a hole transporting layer 30, an emitting layer 40, an electron transporting layer 50, and a cathode 60 are stacked on a substrate (not shown) in this order. In this device, the organic thin layer has a stacked structure of the hole injecting layer 20, the hole transporting layer 30, the emitting layer 40, and the electron transporting layer 50. At least one of the layers constituting the organic thin layers contains the material for an organic EL device of the invention. This structure leads to a lowered driving voltage and a prolonged lifetime of an organic EL device.

The content of the material for an organic EL device in the layer constituting organic thin layers containing the material for an organic EL device of the invention is preferably 1 to 100 mol %.

In the organic EL device of the invention, it is preferred that a layer which is present in a region (hole transporting region) between the anode 10 and the emitting layer 40, specifically, the hole-injection layer 20 or the hole transporting layer 30, contain the material for an organic EL device of the invention. In the device having both the hole injecting layer 20 and the hole transporting layer 30 like the embodiment, it is preferred that the hole-injection layer 20 nearer the anode contain the material for an organic EL device of the invention.

When the material for an organic EL device of the invention is used in the layer present in the hole transporting region, the material for an organic EL device of the invention may form the hole injecting layer or the hole transporting layer singly or in combination with other materials.

For example, when the material for an organic EL device of the invention and an aromatic amine derivative are mixed to form the hole-injection layer or the hole transporting layer, it is preferable to use a phenylenediamine compound represented by the formula (III).

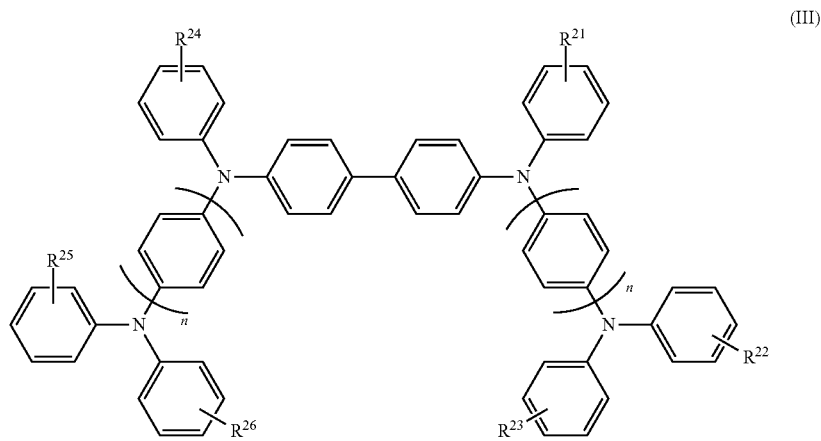

(III)

wherein $R^{21}$ to $R^{26}$ are a hydrogen atom, a halogen atom, a trifluoromethyl group, an alkyl group, an aryl group, or a heterocycle; $R^{21}$ to $R^{26}$ may form a naphthalene skeleton, a carbazole skeleton, or a fluorene skeleton with a phenyl group bonded; and n represents 1 or 2.

If the above phenylenediamine compound is contained in combination, uniformity, heat resistance, or carrier-injection properties of the film may be improved as compared with a case where the material for an organic EL device of the invention is contained singly.

In the formula (III), fluorine is preferable as the halogen atom represented by $R^{21}$ to $R^{26}$.

As the alkyl group represented by $R^{21}$ to $R^{26}$, methyl, isopropyl, tert-butyl, and cyclohexyl are preferred, for example.

As the aryl group represented by $R^{21}$ to $R^{26}$, phenyl, naphthyl, and fluorenyl are preferable, for example. These groups may be substituted with methyl or the like.

As the heterocycle represented by $R^{21}$ to $R^{26}$, pyridine and pyrazine are preferable, for example.

$R^{21}$ to $R^{26}$ may form a naphthalene skeleton, a carbazole skeleton, or a fluorene skeleton with a phenyl group bonded. These skeletons may be substituted with methyl or the like.

The content of the compound represented by the formula (III) in the hole transporting layer or the hole injecting layer is preferably 0.1 to 99 mol %.

Preferred examples of the compound (III) are given below.

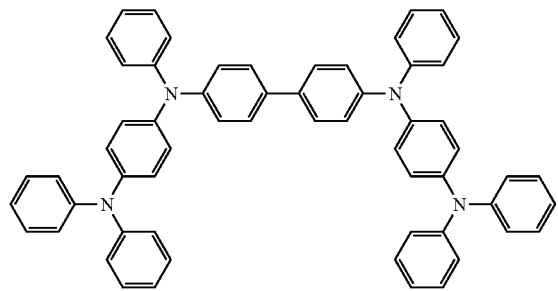 (C-1)
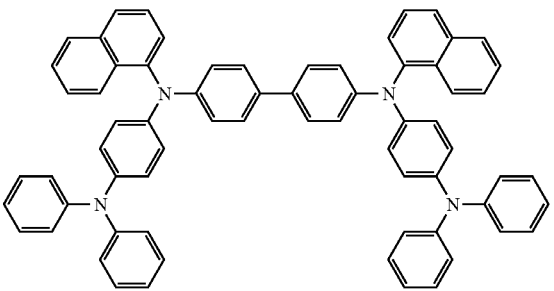 (C-2)
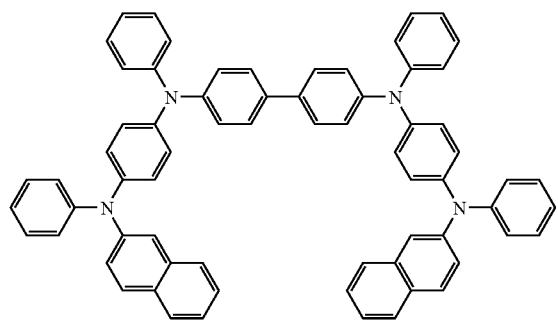 (C-3)
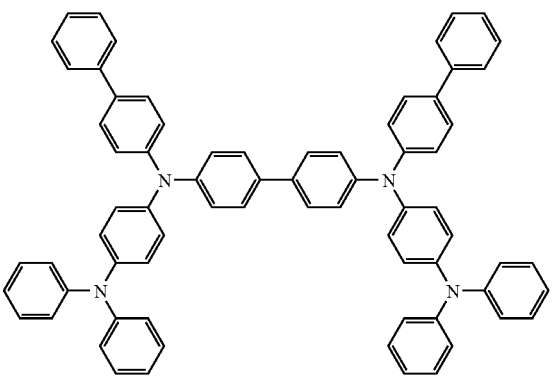 (C-4)
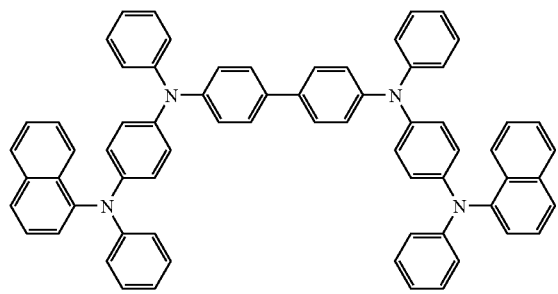 (C-5)
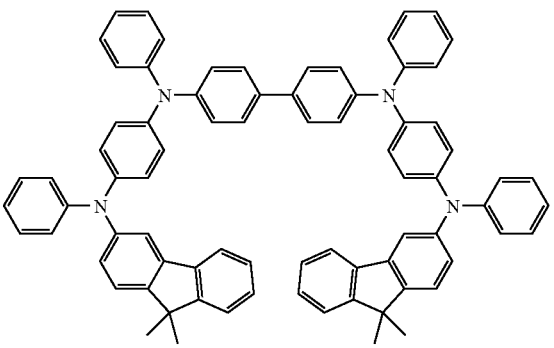 (C-6)
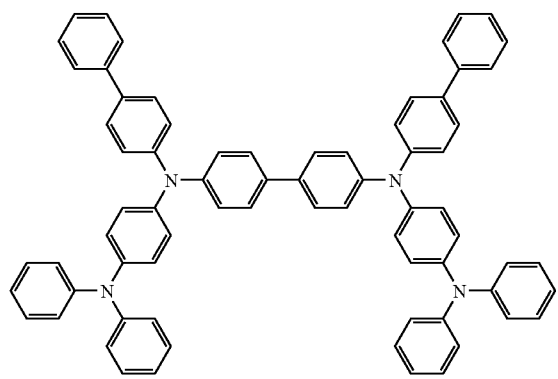 (C-7)
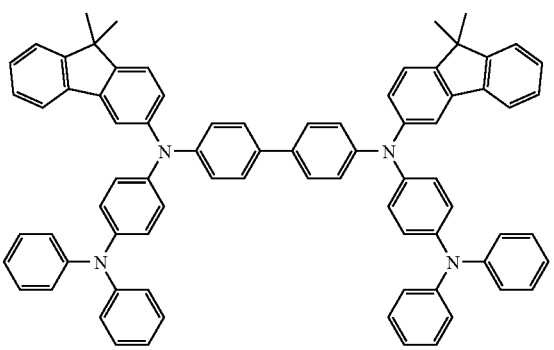 (C-8)

(C-9)
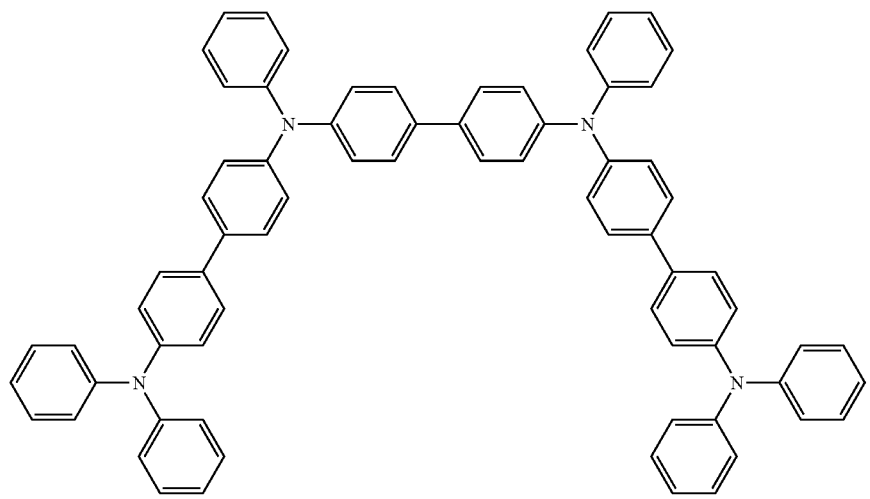
(C-10)
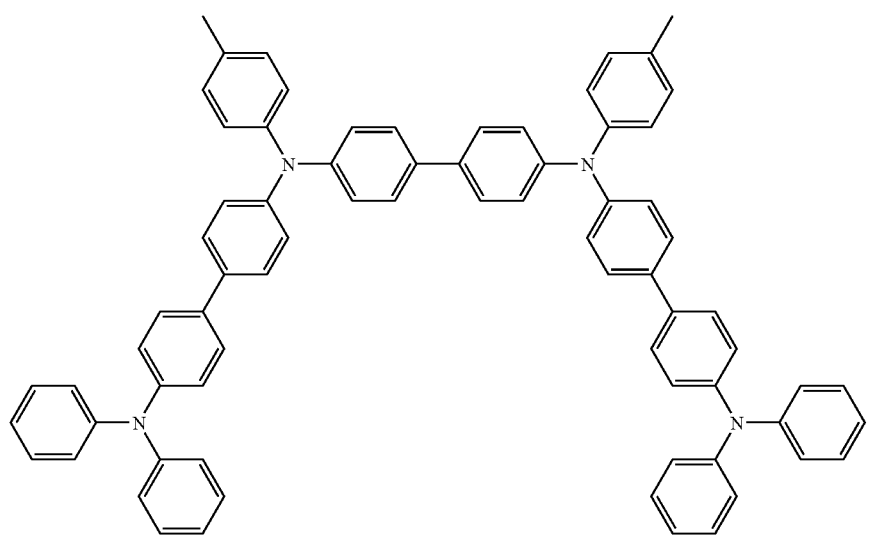
(C-11)
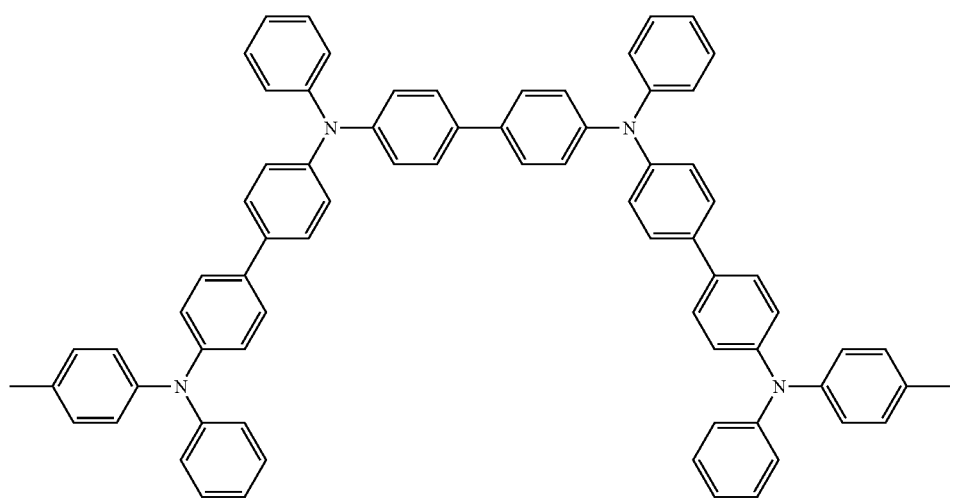

-continued

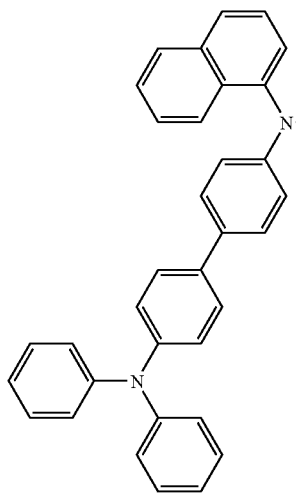 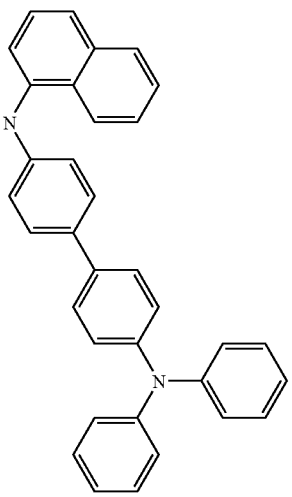

(C-12)

The structure of the organic EL device of the invention is not limited to the embodiment described above. For example, the organic EL device of the invention may have structures (1) to (15) shown below.
(1) Anode/emitting layer/cathode
(2) Anode/emitting layer/cathode
(3) Anode/hole transporting layer/emitting layer/electron injecting layer/cathode
(4) Anode/hole transporting layer/emitting layer/electron transporting layer/cathode
(5) Anode/hole transporting layer/adhesion-improving layer/cathode
(6) Anode/hole injecting layer/hole transporting layer/emitting layer/electron transporting layer/cathode (FIG. 1)
(7) Anode/hole transporting layer/emitting layer/electron transporting layer/electron injecting layer/cathode
(8) Anode/hole injecting layer/hole transporting layer/emitting layer/electron transporting layer/electron injecting layer/cathode
(9) Anode/insulative layer/hole transporting layer/emitting layer/electron transporting layer/cathode
(10) Anode/hole transporting layer/emitting layer/electron transporting layer/insulative layer/cathode
(11) Anode/inorganic semiconductor layer/insulative layer/hole transporting layer/emitting layer/insulative layer/cathode
(12) Anode/insulative layer/hole transporting layer/emitting layer/electron transporting layer/insulative layer/cathode
(13) Anode/hole injecting layer/hole transporting layer/emitting layer/electron transporting layer/insulative layer/cathode
(14) Anode/insulative layer/hole injecting layer/hole transporting layer/emitting layer/electron transporting layer/electron injecting layer/cathode
(15) Anode/insulative layer/hole injecting layer/hole transporting layer/emitting layer/electron transporting layer/electron injecting layer/insulative layer/cathode Of these, the structures (4), (6), (7), (8), (12), (13), and (15) are preferably used.

Each member constituting the organic EL device of the invention will be described below.

[Transparent Substrate]

The organic EL device of the invention is formed on a transparent substrate. The transparent substrate is a substrate for supporting the organic EL device, and is preferably a flat and smooth substrate having a transmittance of 50% or more to light rays within visible ranges of 400 to 700 nm.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Transparency is not required when the supporting substrate is positioned in an area opposite to the outcoupling direction.

[Anode]

The anode of the organic EL device plays a role for injecting holes into its hole transporting layer or emitting layer. When transparency is required in an area nearer to the anode, indium tin oxide alloy (ITO), tin oxide (NESA), zinc tin oxide alloy (IZO), gold, silver, platinum, copper, and the like may be used as the material for the anode. When a reflective anode which does not require transparency is used, a metal such as aluminum, molybdenum, chromium, and nickel or alloys may be used.

Although these materials may be used individually, alloys thereof or materials wherein another element is added to the materials can be appropriately selected for use.

In the case where emission from the emitting layer is outcoupled through the anode, the transmittance of the anode to the emission is preferably more than 10%. The sheet resistance of the anode is preferably several hundreds $\Omega/\square$ or less. The film thickness of the anode, which is varied depending upon the material thereof, is usually from 10 nm to 1 μm, preferably from 10 to 200 nm.

[Emitting Layer]

The emitting layer of the organic EL device has the following functions (1) to (3) in combination.
(1) Injecting function: function of allowing injection of holes from anode or hole injecting layer and injection of electrons from cathode or electron injecting layer upon application of electric field
(2) Transporting function: function of moving injected carriers (electrons and holes) due to force of electric field
(3) Emitting function: function of providing a site for recombination of electrons and holes to emit light Note that electrons and holes may be injected into the emitting layer with different degrees, or the transportation capabilities indicated by the mobility of holes and electrons may differ. It is preferable that the emitting layer move either electrons or holes.

As the emitting material or the doping material used for the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, a quinoline metal complex, an aminoquinoline metal complex, a benzoquinoline metal complex, imine, diphenyl ethylene, vinylanthracene, diaminocarbazol, pyran, thiopyran, polymethine, merocyanine, an imidazole chelate oxanoid compound, quinacridone, rubrene, a fluorescent pigment and like can be given. Note that the emitting material and the doping material are not limited to these compounds.

As the host material used for the emitting layer, the compounds represented by the following formulas (i) to (ix) are preferable.

Asymmetrical anthrathene represented by the following formula (i)

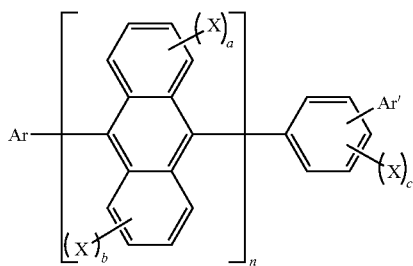

(i)

wherein Ar is a substituted or unsubstituted condensed aromatic group having 10 to 50 nucleus carbon atoms, Ar' is a substituted or unsubstituted aromatic group having 6 to 50 nucleus carbon atoms, X is a substituted or unsubstituted aromatic group having 6 to 50 nucleus carbon atoms, substituted or unsubstituted aromatic heterocyclic group having 5 to 50 nucleus atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus atoms, a substituted or unsubstituted arythio group having 5 to 50 nucleus atoms, a substituted or unsubstituted alkoxycarbonyl group having 1 to 50 carbon atoms, a carboxyl group, a halogen atom, a cyano group, a nitro group or a hydroxyl group.

a, b and c are each an integer of 0 to 4. n is an integer of 1 to 3. When n is two or more, the groups in [ ] may be the same or different.

Asymmetrical monoanthrathene derivatives represented by the following formula (ii)

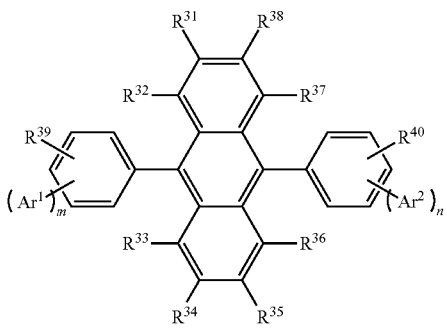

(ii)

wherein $Ar^1$ and $Ar^2$ are independently a substituted or unsubstituted aromatic ring group having 6 to 50 nucleus carbon atoms, and m and n are each an integer of 1 to 4, provided that in the case where m=n=1 and Ar1 and $Ar^2$ are symmetrically bonded to the benzene rings, $Ar^1$ and $Ar^2$ are not the same, and in the case where m or n is an integer of 2 to 4, m is different from n, $R^{31}$ to $R^{40}$ are independently a hydrogen atom, a substituted or unsubstituted aromatic ring group having 6 to 50 nucleus carbon atoms, a substituted or unsubstituted aromatic hetrocyclic group having 5 to 50 nucleus atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus atoms, a substituted or unsubstituted arylthio group having 5 to 50 nucleus atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives represented by the following Formula (iii)

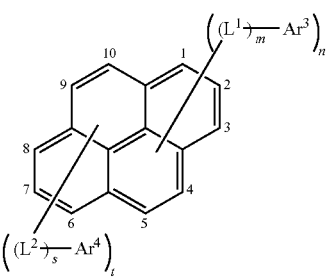

(iii)

wherein $Ar^3$ and $Ar^4$ are each a substituted or unsubstituted aromatic group having 6 to 50 nucleus carbon atoms;

$L^1$ and $L^2$ are each a substituted or unsubstituted phenylene group, a substituted or unsubstituted naphthalenylene group, a substituted or unsubstituted fluolenylene group, or a substituted or unsubstituted dibenzosilolylene group;

m is an integer of 0 to 2, n is an integer of 1 to 4, s is an integer of 0 to 2, and t is an integer of 0 to 4;

$L^1$ or $Ar^3$ bonds at any one position of 1 to 5 of the pyrene, and $L^2$ or $Ar^4$ bonds at any one position of 6 to 10 of the pyrene;

provided that when n+t is an even number, $Ar^3$, $Ar^4$, $L^1$ and $L^2$ satisfy the following (1) and (2):

(1) $Ar^3 \neq Ar^4$ and/or $L^1 \neq L^2$ where ≠ means these substituents are groups having different structures from each other.

(2) when $Ar^3=Ar^4$ and $L^1=L^2$, (2-1) m≠s and/or n≠t, or (2-2) when m=s and n=t, (2-2-1) $L^1$ and $L^2$, or the pyrene each bond to $Ar^3$ and $Ar^4$ at different positions, or (2-2-2) when $L^1$ and $L^2$, or the pyrene each bond to $Ar^3$ and $Ar^4$ at the same positions, the pyrene is neither substituted by $L^1$ and $L^2$, or $Ar^3$ and $Ar^4$ at 1 and 6 positions, nor 2 and 7 positions.

Asymmetrical anthrathene represented by the following formula (iv)

(iv)

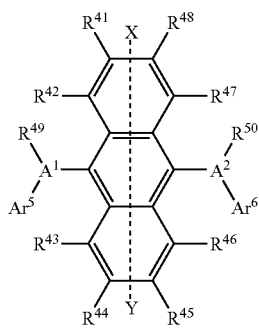

wherein $A^1$ and $A^2$ are independently a substituted or unsubstituted condensed aromatic ring group having 10 to 20 nucleus carbon atoms, $Ar^5$ and $Ar^6$ are independently a hydrogen atom or a substituted or unsubstituted aromatic ring group with 6 to 50 nucleus carbon atoms, $R^{41}$ to $R^{50}$ are independently a hydrogen atom or a substituted or unsubstituted aromatic ring group having 6 to 50 nucleus carbon atoms, a substituted or unsubstituted aromatic hetrocyclic group having 5 to 50 nucleus atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nucleus atoms, a substituted or unsubstituted arylthio group having 5 to 50 nucleus atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^5$, $Ar^6$, $R^{49}$ and $R^{50}$ may be plural, and adjacent groups thereof may form a saturated or unsaturated ring structure, provided that in the formula (iv), groups do not symmetrically bond to 9 and 10 positions of the central anthracene with respect to X-Y axis.

Anthrathene derivative represented by the following formula (v)

(v)

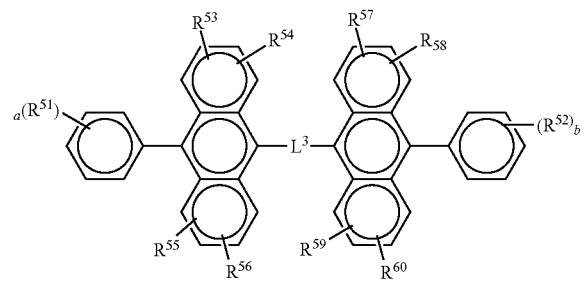

wherein $R^{51}$ to $R^{60}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are each an integer of 1 to 5; when they are 2 or more, $R^{51}$s or $R^{52}$s may be the same or different, or $R^{51}$s or $R^{52}$s may be bonded together to form a ring; $R^{53}$ and $R^{54}$, $R^{55}$ and $R^{56}$, $R^{57}$ and $R^{58}$, or $R^{59}$ and $R^{60}$ may be bonded together to form a ring; and $L^3$ is a single bond, —O—, —S—, —N(R)— (R is an alkyl group or a substituted or unsubstituted aryl group), an alkylene group or an arylene group.

Anthrathene derivative represented by the following formula (vi)

(vi)

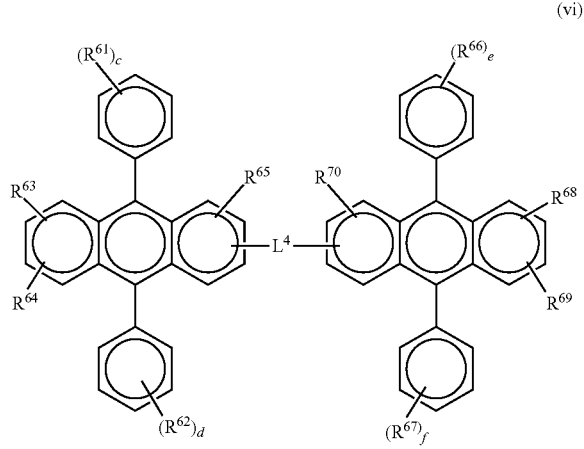

wherein $R^{61}$ to $R^{70}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are each an integer of 1 to 5; when they are 2 or more, $R^{61}$s, $R^{62}$s, $R^{66}$s or $R^{67}$s may be the same or different, $R^{61}$s, $R^{62}$s, $R^{66}$s or $R^{67}$s may be bonded together to form a ring, or $R^{63}$ and $R^{64}$, or $R^{68}$ and $R^{69}$ may be bonded together to form a ring; and $L^4$ is a single bond, —O—, —S—, —N(R)— (R is an alkyl group or a substituted or unsubstituted aryl group), an alkylene group or an arylene group.

Spirofluorene derivatives represented by the following formula (vii)

(vii)

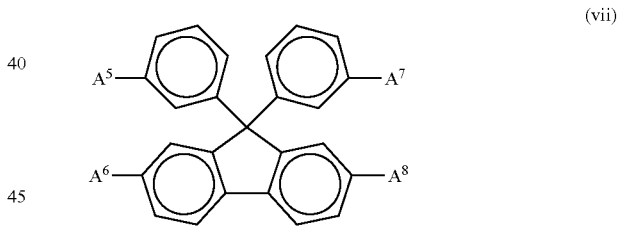

wherein $A^5$ to $A^8$ are each independently a substituted or unsubstituted biphenyl group or a substituted or unsubstituted naphthyl group.

Condensed ring-containing compounds represented by the following formula (viii)

(viii)

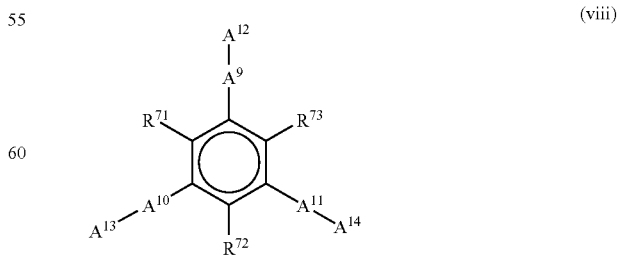

wherein $A^9$ to $A^{14}$ are the same as the above-described ones and $R^{71}$ to $R^{73}$ are individually a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^9$ to $A^{14}$ is a group having a condensed aromatic ring with three or more rings.

Fluorene compounds represented by the following formula (ix)

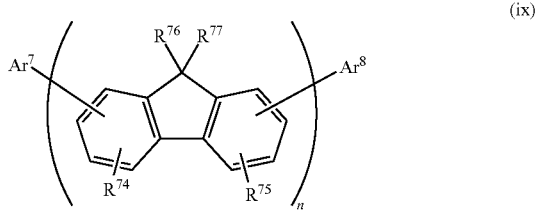

wherein $R^{74}$ and $R^{75}$ are a hydrogen atom, a substituted or unsubstituted alkyl group, substituted or unsubstituted aralkyl group, substituted or unsubstituted aryl group, substituted or unsubstituted heterocyclic group, substituted amino group, cyano group, or a halogen atom. $R^{74}$s or $R^{74}$s bonded to different fluorene groups may be the same or different, and $R^{74}$ and $R^{75}$ bonded to a single fluorene group may be the same or different. $R^{76}$ and R77 are a hydrogen atom, a substituted or unsubstituted alkyl group, substituted or unsubstituted aralkyl group, substituted or unsubstituted aryl group, or substituted or unsubstituted heterocyclic group, provided that $R^{76}$s or $R^{77}$s bonded to different fluorene groups may be the same or different, and $R^{76}$ and $R^{77}$ bonded to a single fluorene group may be the same or different. $Ar^7$ and $Ar^8$ are a substituted or unsubstituted condensed polycyclic aromatic group with a total number of benzene rings of three or more or a condensed polycyclic heterocyclic group which is bonded to the fluorene group through substituted or unsubstituted carbon and has a total number of benzene rings and heterocyclic rings of three or more, provided that $Ar^7$ and $Ar^8$ may be the same or different. n is an integer of 1 to 10.

Among the above compounds, the host material is preferably the anthracene derivative, more preferably the monoanthracene derivative, and particularly the asymmetrical anthracene.

Phosphorescent compounds can be used as a dopant of an emitting material.

When using a phosphorescent compound, compounds containing a carbazole ring are preferred for a host material.

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable.

The compounds containing a carbazole ring, which are a host suitable for phosphorescence emission, is a compound which allows a phosphorescent compound to emit as a result of energy transfer from its excited state to the phosphorescent compound. A host compound is not limited so long as the compound can transfer its excited energy to a phosphorescent compound and it can be selected depending on purposes. The host compound may contain any hetrocyclic ring other than a carbazole ring.

Specific examples of the host compounds include carbazole, triazole, oxazole, oxadiazole, imidazole, polyarylalkane, pyrazoline, pyrazolone, phenylanediamine, arylamine, amino-substituted calcone, styryl anthracene, fluorenone, hydrazone, stilbene and silazane derivatives; aromatic tertiary amine, styrylamine, aromatic dimethylidene and porphyrin compounds; anthraquinodimethane, anthrone, diphenylquinone, thiopyrandioxide, carbodiimide, fluoreniridenemethane and distyrylpyrazine derivatives; heterocyclic tetracarboxylic anhydrides such as naphthaleneperylene; phthalocyanine derivatives; metal complexes of 8-quinolinol derivatives; various metal complex polysilane compounds represented by metal complexes having metalphthalocyanine, benzoxazole or benzothiaole as a ligand; electroconductive macromolecular oligomers such as poly (N-vinylcarbazole) derivatives, aniline copolymers, thiophene oligomers and polythiophene; and macromolecular compounds such as polythiophene, polyphenylene, polyphenylenevinylene and polyfluorene derivatives. Host compounds can be used individually or as a combination of two or more kinds.

Specific compounds shown below can be exemplified.

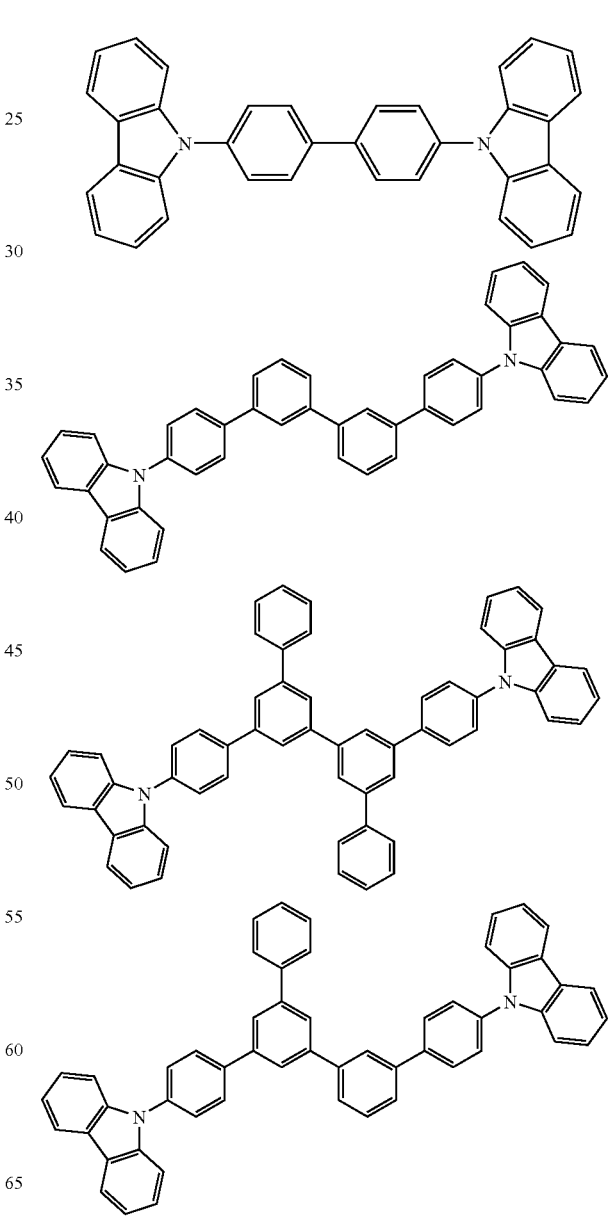

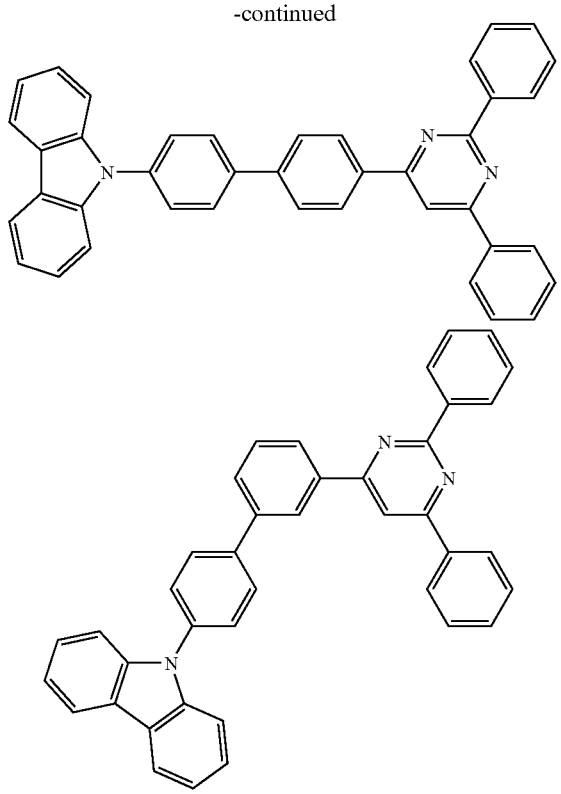

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. As a porphyrin metal complex, a porphyrin platinum complex is preferable. The phosphorescent compounds can be used individually or as a combination of two or more kinds.

There are various ligands forming an ortho-metalated metal complex. Preferable ligands include 2-phenylpyridine, 7,8-benzoquinoline, 2-(2-thienyl)pyridine, 2-(1-naphtyl)pyridine and 2-phenylquinoline derivatives. These derivatives may have substituents if necessary. Fluorides and derivatives with a trifluoromethyl group introduced are particularly preferable as a blue dopant. As an auxiliary ligand, preferred are ligands other than the above-mentioned ligands, such as acetylacetonate and picric acid may be contained.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

The emitting layer may contain hole transporting materials, electron transporting materials and polymer binders if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

[Hole Injecting/Transporting Layer]

The hole injecting/transporting layer is a layer for helping the injection of holes into the emitting layer to transport the holes to a light emitting region. The hole mobility thereof is large and the ionization energy thereof is usually as small as 5.5 eV or less. Such a hole injecting/transporting layer is preferably made of a material which can transport holes to the emitting layer at a lower electric field intensity. The hole mobility thereof is preferably at least $10^{-4}$ cm$^2$/V·second when an electric field of, e.g., $10^4$ to $10^6$ V/cm is applied.

As mentioned above, when the material for an organic EL device of the invention in the hole transporting region, the hole transporting layer may be formed using the compound of the invention singly or in combination with other materials. When the hole transporting layer is formed using a mixture, it is preferable to mix a phenylenediamine compound represented by the above formula (III).

However, a compound to be mixed is not limited to the compound represented by the formula (III). A suitable compound may be appropriately selected from compounds generally used as the carrier-transporting material for the hole or known compounds used in the hole injecting layer of an EL device.

When a region other than the hole transporting region includes the material of the invention, the hole transporting layer may be formed using the following mixed materials singly.

Specific examples of mixed materials include triazole derivatives (see U.S. Pat. No. 3,112,197 or the like), oxadiazole derivatives (see U.S. Pat. No. 3,189,447 or the like), imidazole derivatives (see JP-B-37-16096 or the like), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, or the like), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, or the like), phenylenediamine derivatives (see U.S. Pat. No. 3,615,404, JP-B-51-10105, 46-3712 and 47-25336, JP-A-54-53435, 54-110536 and 54-119925, or the like), arylamine derivatives (see U.S. Pat. Nos. 3,567,450, 3,180,703, 3,240,597, 3,658,520, 4,232,103, 4,175,961 and 4,012,376, JP-B-49-35702 and 39-27577, JP-A-55-144250, 56-119132 and 56-22437, DE1,110,518, or the like), amino-substituted chalcone derivatives (see U.S. Pat. No. 3,526,501, or the like), oxazole derivatives (ones disclosed in U.S. Pat. No. 3,257,203, or the like), styrylanthracene derivatives (see JP-A-56-46234, or the like), fluorenone derivatives (JP-A-54-110837, or the like), hydrazone derivatives (see U.S. Pat. Nos. 3,717,462, JP-A-54-59143, 55-52063, 55-52064, 55-46760, 55-85495, 57-11350, 57-148749 and 2-311591, or the like), stilbene derivatives (see JP-A-61-210363, 61-228451, 61-14642, 61-72255, 62-47646, 62-36674, 62-10652, 62-30255, 60-93455, 60-94462, 60-174749 and 60-175052, or the like), silazane derivatives (U.S. Pat. No. 4,950,950), polysilanes (JP-A-2-204996), aniline copolymers (JP-A-2-282263), and electroconductive high molecular oligomers (in particular thiophene oligomers) disclosed in JP-A-1-211399.

Other than the hole transporting layer, in order to help the injection of holes, it is preferred that the hole injecting layer be provided separately. As the material for the hole injecting layer, the material of the organic EL of the invention may be used singly or in combination with other materials. As the other materials, the same materials used for the hole transporting layer can be used. The following can also be used, other than the compound shown in the above formula (III):

porphyrin compounds (disclosed in JP-A-63-2956965 or the like), aromatic tertiary amine compounds, and styrylamine compounds (see U.S. Pat. No. 4,127,412, JP-A-53-27033, 54-58445, 54-149634, 54-64299, 55-79450, 55-144250, 56-119132, 61-295558, 61-98353 and 63-295695, or the like). Of these, the aromatic tertiary amine compounds are particularly preferable.

The following can also be given as examples: 4,4'-bis(N-(1-naphthyl)-N-phenylamino)biphenyl, which has in the molecule thereof two condensed aromatic rings, disclosed in U.S. Pat. No. 5,061,569, 4,4',4"-tris(N-(3-methylphenyl)-N-phenylamino)triphenylamine, wherein three triphenylamine units are linked to each other in a star-burst form, disclosed in JP-A-4-308688, and the like.

Other than the aromatic dimethylidene type compounds, inorganic compounds such as p-type Si and p-type SiC can also be used as the material for the hole injecting layer or the hole transporting layer.

The film thickness of the hole injecting/transporting layer is not particularly limited, and is usually from 5 nm to 5 μm. This hole injecting layer or the hole transporting layer may be a single layer made of one or more of the above-mentioned materials, or may be stacked hole injecting layers or hole transporting layers made of different compounds, insofar as the compound of the invention is contained.

The organic semiconductor layer, which is a part of the hole transporting layer, is a layer for helping the injection of holes or electrons into the emitting layer, and is preferably a layer having an electric conductivity of $10^{-10}$ S/cm or more. As the material for such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

[Electron Injecting/transporting Layer]

A hole injecting, transporting layer is a layer for helping the injection of holes into the emitting layer so as to transport the holes to an emitting region, and exhibits a high electron mobility. An adhesion-improving layer is formed of a material which exhibits excellent adhesion to the cathode.

The thickness of the electron transporting layer is arbitrarily selected in the range of several nanometers to several micrometers. When the electron transporting layer has a large thickness, it is preferable that the electron mobility be at least $10^{-5}$ cm$^2$/Vs or more at an applied electric field of $10^4$ to $10^6$ V/cm in order to prevent an increase in voltage.

As the material used for the electron injecting layer, 8-hydroxyquinoline, a metal complex of an 8-hydroxyquinoline derivative, and an oxadiazole derivative are suitable. As specific examples of 8-hydroxyquinoline and a metal complex of an 8-hydroxyquinoline derivative, metal chelate oxinoid compounds including a chelate of oxine (8-quinolinol or 8-hydroxyquinoline) can be given. For example, tris(8-hydroxyquinolinol)aluminum may be used as an electron injecting material.

An electron transporting compound of the following formula can be given as the oxadiazole derivative.

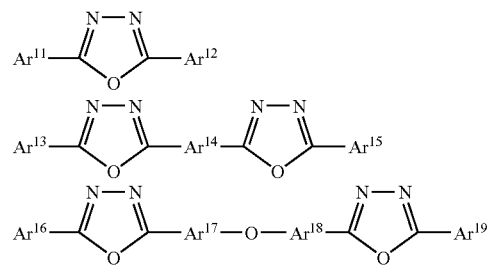

wherein $Ar^{11}$, $Ar^{12}$, $Ar^{13}$, $Ar^{15}$, $Ar^{16}$, and $Ar^{19}$ are independently substituted or unsubstituted aryl groups and may be the same or different. $Ar^{14}$, $Ar^{17}$, and $Ar^{18}$ are independently substituted or unsubstituted arylene groups and may be the same or different.

As examples of the aryl group, a phenyl group, a biphenyl group, an anthryl group, a perylenyl group, and a pyrenyl group can be given. As examples of the arylene group, a phenylene group, a naphthylene group, a biphenylene group, an anthrylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron transporting compound is preferably one from which a thin film can be formed.

The following compounds can be given as specific examples of the electron transporting compound.

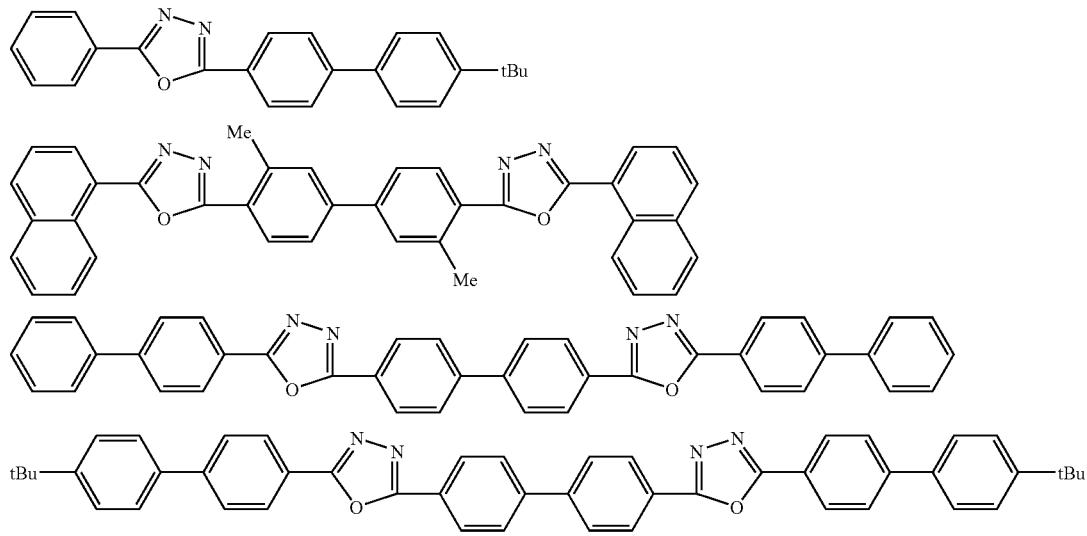

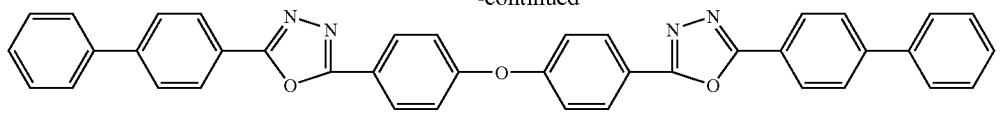

Furthermore, as materials used for the electron injecting layer and electron transporting layer, the compounds represented by the following formulas (1) to (6) may be used.

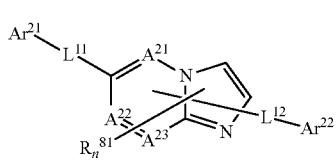 (1)

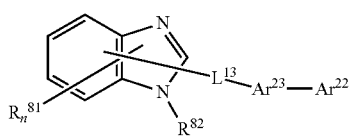 (2)

Nitrogen-containing heterocyclic ring derivatives represented by the formulas (1) and (2) wherein $A^{21}$ to $A^{23}$ are each independently a nitrogen atom or a carbon atom;

$Ar^{21}$ is a substituted or unsubstituted aryl group having 6 to 60 nucleus carbon atoms or a substituted or unsubstituted heteroaryl group having 3 to 60 nucleus carbon atoms; $Ar^{22}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, a substituted or unsubstituted alkoxy group having 1 to 20 carbon atoms, or a divalent group of these; provided that one of $Ar^{21}$ and $Ar^{22}$ is a substituted or unsubstituted condensed ring group having 10 to 60 nucleus carbon atoms, a substituted or unsubstituted monohetero condensed ring group having 3 to 60 nucleus carbon atoms, or a divalent group of these;

$Ar^{23}$ is a substituted or unsubstituted arylene group having 6 to 60 carbon atoms or a substituted or unsubstituted heteroarylene group having 3 to 60 carbon atoms;

$L^{11}$, $L^{12}$, and $L^{13}$ are each individually a single bond, a substituted or unsubstituted arylene group having 6 to 60 nucleus carbon atoms, a substituted or unsubstituted heteroarylene group having 3 to 60 nucleus carbon atoms or a substituted or unsubstituted fluorenylene group;

$R^{81}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of $R^{81}$s may be the same or different; adjacent $R^{81}$s may be bonded to form a carbocyclic aliphatic ring or a carbocyclic aromatic ring; and $R^{82}$ is a hydrogen atom, a substituted or unsubstituted aryl group having 6 to 60 nucleus carbon atoms, a substituted or unsubstituted heteroaryl group having 3 to 60 nucleus carbon atoms, a substituted or unsubstituted alkyl group having 1 to 20 carbon atoms, a substituted or unsubstituted alkoxy group having 1 to 20 carbon atoms or -$L^{11}$-$Ar^{21}$—$Ar^{22}$.

$HAr\text{-}L^{14}\text{-}Ar^{24}\text{—}Ar^{25}$ (3)

Nitrogen-containing heterocyclic ring derivatives represented by the formula (3) wherein HAr is a nitrogen-containing heterocyclic ring with 3 to 40 carbon atoms which may have a substituent; $L^{14}$ is a single bond, an arylene group with 6 to 60 carbon atoms which may have a substituent, a heteroarylene group with 3 to 60 carbon atoms which may have a substituent or a fluorenylene group which may have a substituent; $Ar^{24}$ is a divalent aromatic hydrocarbon group with 6 to 60 carbon atoms which may have a substituent; and $Ar^{25}$ is an aryl group with 6 to 60 carbon atoms which may have a substituent or a heteroaryl group with 3 to 60 carbon atoms which may have a substituent.

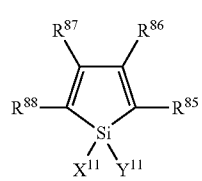 (4)

Silacyclopentadiene derivatives represented by the formula (4) wherein $X^{11}$ and $Y^{11}$ are individually a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or $X^{11}$ and $Y^{11}$ are bonded to form a saturated or unsaturated ring, and $R^{85}$ to $R^{88}$ are individually hydrogen, halogen, a substituted or unsubstituted aryl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or adjacent groups of $R^{85}$ to $R^{88}$ from a substituted or unsubstituted condensed ring.

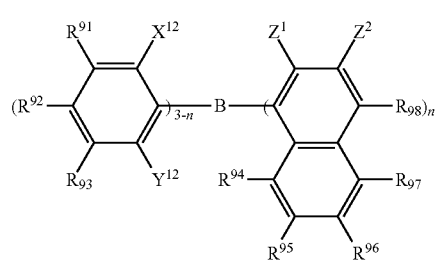 (5)

Borane derivatives represented by the formula (5) wherein $R^{91}$ to $R^{98}$ and $Z^{2}$ are individually a hydrogen atom, a saturated or unsaturated hydrocarbon group, an aromatic group, a heterocyclic group, a substituted amino group, a substituted boryl group, an alkoxy group, or an aryloxy group, $X^{12}$, $Y^{12}$, and $Z^1$ are individually a saturated or unsaturated hydrocarbon group, an aromatic group, a heterocyclic group, a substituted amino group, an alkoxy group, or an aryloxy group, the substituents for $Z^1$ and $Z^2$ may be bonded to form a condensed ring, n is an integer of 1 to 3, provided that the $Z^1$s may differ when n is 2 or more, and a case in which n is 1, $X^{12}$, $Y^{12}$, and $R^{92}$ are methyl groups, and $R^{98}$ is a hydrogen atom or a substituted boryl group, and a case in which n is 3 and $Z^1$ is a methyl group are excluded.

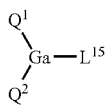

(6)

wherein $Q^1$ and $Q^2$ are individually ligands of the following formula (7), $L^{15}$ is a ligand represented by a halogen atom, a substituted or unsubstituted alkyl group, a substituted or unsubstituted cycloalkyl group, a substituted or unsubstituted aryl group, a substituted or unsubstituted heterocyclic ring group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group), or —O—Ga—$Q^3$ ($Q^4$) ($Q^3$ and $Q^4$ have the same meanings as $Q^1$ and $Q^2$)

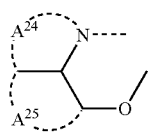

(7)

wherein the rings $A^{24}$ and $A^{25}$ are condensed six-membered aryl ring structure which may have a substituent.

The metal complexes have the strong nature of an n-type semiconductor and large ability of injecting electrons. Further the energy generated at the time of forming a complex is small so that a metal is then strongly bonded to ligands in the complex formed and the fluorescent quantum efficiency becomes large as the emitting material.

Specific examples of the rings $A^{24}$ and $A^{25}$ which form the ligands of the formula (7) include halogen atoms such as chlorine, bromine, iodine and fluorine; substituted or unsubstituted alkyl groups such as methyl, ethyl, propyl, butyl, sec-butyl, tert-butyl, pentyl, hexyl, heptyl, octyl, stearyl and trichloromethyl; substituted or unsubstituted aryl groups such as phenyl, naphthyl, 3-methylphenyl, 3-methoxyphenyl, 3-fluorophenyl, 3-trichloromethylphenyl, 3-trifluoromethylphenyl and 3-nitrophenyl; substituted or unsubstituted alkoxy groups such as methoxy, n-butoxy, tert-butoxy, trichloromethoxy, trifluoroethoxy, pentafluoropropoxy, 2,2,3,3-tetrafluoropropoxy, 1,1,1,3,3,3-hexafluoro-2-propoxy and 6-(perfluoroethyl)hexyloxy; substituted or unsubstituted aryloxy groups such as phenoxy, p-nitrophenoxy, p-tert-butylphenoxy, 3-fluorophenoxy, pentafluorophenyl and 3-trifluoromethylphenoxy; substituted or unsubstituted alkylthio groups such as methythio, ethylthio, tert-butylthio, hexylthio, octylthio and trifruoromethyltio; substituted or unsubstituted arylthio groups such as phenylthio, p-nitrophenylthio, p-tert-butylphenylthio, 3-fluorophenylthio, pentafluorophenylthio and 3-trifluoromethylphenylthio; a cyano group; a nitro group, an amino group; mono or di-substituted amino groups such as methylamino, dimethylamino, ethylamino, diethylamino, dipropylamino, dibutylamino and diphenylamino; acylamino groups such as bis(acetoxymethyl)amino, bis(acetoxyethyl)amino, bis(acetoxypropyl)amino and bis(acetoxybutyl)amino; a hydroxy group; a siloxy group; an acyl group; substituted or unsubstituted carbamoyl groups such as carbamoyl, methylcarbamoyl, dimethylcarbamoyl, ethylcarbamoyl, diethylcarbamoyl, propylcarbamoyl, butylcarbamoyl and phenylcarbamoyl; a carboxylic group; a sulfonic acid group; an imido group; cycloalkyl groups such as cyclopentyl and cyclohexyl; aryl groups such as phenyl, naphthyl, biphenyl, anthryl, phenanthryl, fluorenyl and pyrenyl; and heterocyclic groups such as pyridinyl, pyrazinyl, pyrimidinyl, pryidazinyl, triazinyl, indolinyl, quinolinyl, acridinyl, pyrrolidinyl, dioxanyl, piperidinyl, morpholidinyl, piperazinyl, triathinyl, carbazolyl, furanyl, thiophenyl, oxazolyl, oxadiazolyl, benzooxazolyl, thiazolyl, thiadiazolyl, benzothiazolyl, triazolyl, imidazolyl, benzoimidazolyl and puranyl. Moreover the above-mentioned substituents may be bonded to each other to form a six-membered aryl or heterocyclic ring.

A preferred embodiment of the invention is a device containing a reducing dopant in an interfacial region between its electron transferring region or cathode and organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Li (work function: 2.9 eV), Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are in particular preferred.

Of these, a more preferable reducing dopant is at least one alkali metal selected from the group consisting of K, Rb and Cs. Even more preferable is Rb or Cs. Most preferable is Cs.

These alkali metals are particularly high in reducing ability. Thus, the addition of a relatively small amount thereof to an electron injecting zone makes it possible to improve the luminance of the organic EL device and make the lifetime thereof long. As the reducing dopant having a work function of 2.9 eV or less, any combination of two or more out of these alkali metals is also preferred. Particularly preferred is any combination containing Cs, for example, combinations of Cs and Na, Cs and K, Cs and Rb, or Cs, Na and K.

The combination containing Cs makes it possible to exhibit the reducing ability efficiently. The luminance of the organic EL device can be improved and the lifetime thereof can be made long by the addition thereof to its electron injecting zone.

In the invention, an electron injecting layer made of an insulator or a semiconductor may further be provided between a cathode and an organic layer. By providing the layer, current leakage can be effectively prevented to improve the injection of electrons.

As the insulator, at least one metal compound selected from the group consisting of alkali metal calcogenides, alkaline earth metal calcogenides, halides of alkali metals and halides of alkaline earth metals can be preferably used. When the electron injecting layer is formed of the alkali metal calcogenide or the like, the injection of electrons can be preferably further improved.

Specifically preferable alkali metal calcogenides include $Li_2O$, $LiO$, $Na_2S$, $Na_2Se$ and $NaO$ and preferable alkaline earth metal calcogenides include CaO, BaO, SrO, BeO, BaS and CaSe. Preferable halides of alkali metals include LiF, NaF, KF, LiCl, KCl, and NaCl. Preferable halides of alkaline earth metals include fluorides such as $CaF_2$, $BaF_2$, $SrF_2$, and $MgF_2$ and $BeF_2$ and halides other than fluorides.

Examples of the semiconductor for forming an electron injecting layer include oxides, nitrides or oxynitrides containing at least one element selected from Ba, Ca, Sr, Yb, Al, Ga, In, Li, Na, Cd, Mg, Si, Ta, Sb and Zn, and combinations of two or more thereof. The inorganic compound for forming an electron injecting layer is preferably a microcrystalline or amorphous insulating thin film. When an electron injecting layer is formed of the insulating thin film, a more uniform thin film can be formed to reduce pixel defects such as dark spots.

Examples of such an inorganic compound include the above-mentioned alkali metal calcogenides, alkaline earth metal calcogenides, halides of alkali metals, and halides of alkaline earth metals.

[Cathode]

For the cathode, the following may be used: an electrode substance made of a metal, an alloy or an electroconductive compound, or a mixture thereof which has a small work function (4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where emission from the emitting layer is outcoupled through the cathode, it is preferred to make the transmittance of the cathode to the emission larger than 10%.

The sheet resistance of the cathode is preferably several hundreds $\Omega/\square$ or less, and the film thickness thereof is usually from 10 nm to 1 μm, preferably from 50 to 200 nm.

[Insulative Layer]

In the organic EL device, pixel defects based on leakage or a short circuit are easily generated since an electric field is applied to the super thin film. In order to prevent this, it is preferred to insert an insulator thin layer between the pair of electrodes.

Examples of the material used in the insulative layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide.

A mixture or laminate thereof may be used.

[Example of Fabricating Organic EL Device]

The organic EL device can be fabricated by forming an anode and an emitting layer, optionally forming a hole injecting layer and an electron injecting layer if necessary, and further forming a cathode by use of the materials and methods exemplified above. The organic EL device can be fabricated in the order reverse to the above, i.e., the order from a cathode to an anode.

An example of the fabrication of the organic EL device will be described below which has a structure wherein the following are successively formed on a transparent substrate: anode/hole transporting layer/emitting layer/electron transporting layer/cathode.

First, a thin film made of an anode material is formed into a thickness of 1 μm or less, preferably 10 to 200 nm on an appropriate transparent substrate by vapor deposition, sputtering or some other method, thereby forming an anode.

Next, a hole transporting layer is formed on this anode. As described above, the hole transporting layer can be formed by vacuum deposition, spin coating, casting, LB technique, or some other method. Vacuum deposition is preferred since a homogenous film is easily obtained and pinholes are not easily generated.

In the case where the hole transporting layer is formed by vacuum deposition, conditions for the deposition vary depending upon the compound used (materials of the hole transporting layer), the desired crystal structure or recombining structure of the hole transporting layer, or the like. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 5 nm to 5 μm.

Next, an emitting layer is disposed on the hole transporting layer. The emitting layer can also be formed by using a desired organic luminescent material and making the material into a thin film by vacuum deposition, sputtering, spin coating, casting or some other method. Vacuum deposition is preferred since a homogenous film is easily obtained and pinholes are not easily generated. In the case where the emitting layer is formed by vacuum deposition, conditions for the deposition, which vary depending on the compound used, can be generally selected from conditions similar to those for the hole transporting layer.

Next, an electron transporting layer is formed on this emitting layer. Like the hole transporting layer and the emitting layer, the layer is preferably formed by vacuum deposition because a homogenous film is required. Conditions for the deposition can be selected from conditions similar to those for the hole transporting layer and the emitting layer.

Lastly, a cathode is stacked thereon to obtain an organic EL device.

The cathode is made of a metal, and vapor deposition or sputtering may be used. However, vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

A method for forming each of the layers constituting the organic EL device of the invention is not particularly limited. Specifically the layers can be formed by a known method, such as vacuum deposition, molecular beam deposition (MBE method), or coating method such as dipping, spin coating, casting, casting, bar coating and roll coating using a solution obtained by dissolving materials in a solvent.

The film thickness of each of the organic layers in the organic EL device of the invention is not particularly limited. In general, defects such as pinholes are easily generated when the film thickness is too small. Conversely, a high applied voltage becomes necessary, leading to low efficiency, when the film thickness is too large. Usually, therefore, the film thickness is preferably in the range of several nanometers to one micrometer.

The organic EL device emits light when applying a voltage between electrodes. When a DC voltage of 5 to 40 V is applied to the organic EL device, emission can be observed when the polarities of the anode and the cathode are positive and negative, respectively. When a voltage with an opposite polarity is applied, no electric current flows and hence, emission does not occur. When an AC voltage is applied, uniform emission can be observed only when the cathode and the anode have a positive polarity and a negative polarity, respectively. The waveform of the AC applied may be arbitrary.

EXAMPLES

The material for an organic EL device and the organic EL device of the invention will be described in detail referring to the following examples, which should not be construed as limiting the scope of the invention.

The structures of the compounds synthesized or used in the examples are shown below.

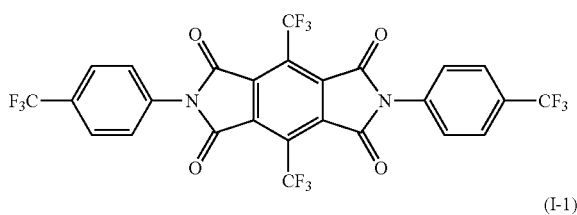
(A-1)

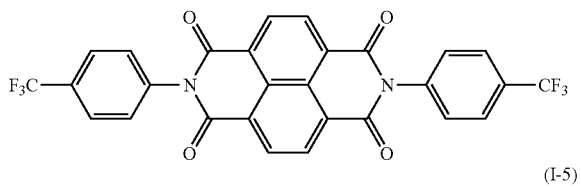
(I-1)

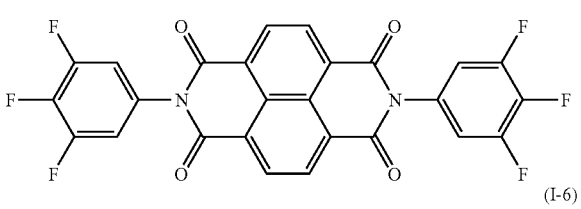
(I-5)

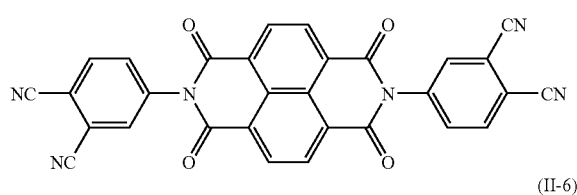
(I-6)

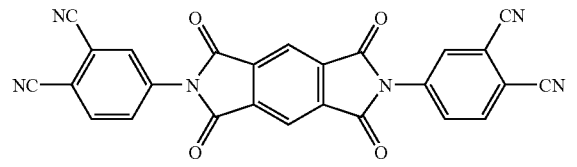
(II-6)

[Material for Organic EL Device]

Example 1

Synthesis of (A-1)

3 g of 1,4-bis(trifluoromethyl)-2,3,5,6-benzene tetracarboxylic anhydride synthesized according to the document (Macromolecules, 25, 3540, 1992) and 2.7 g of 4-(trifluoromethyl) aniline were dissolved in 50 ml of dimethylacetamide. Under a nitrogen atmosphere, the resultant mixture was stirred at room temperature for 1 hour and then heated at 150° C. for six hours with stirring. After cooling, a precipitated solid was washed with hot acetonitrile, followed by sublimation and purification, whereby 2.5 g of a white solid of (A-1) was obtained.

As a result of an IR measurement of the compound obtained, absorption of a carbonyl group at 1715 cm$^{-1}$ was determined. Mass spectrometry revealed that the compound had a peak at an M/Z of 640.

The compound obtained was dissolved in acetonitrile at a concentration of 0.01 mol/l. A reduction potential was measured by cyclic voltammetry using tetrabutylammonium perchlorate (TBAP) as a supporting electrode and a saturated calomel electrode (SCE) as a reference electrode. The reduction potential was found to be 0.3 V.

The reduction potential was measured by cyclic voltammetry in the same manner mentioned above except that the solvent was changed to dimethyl formamide (DMF), and was found to be 0.21 V.

Example 2

Synthesis of (I-1)

5.1 g of naphthalene tetracarboxylic anhydride was added to 45 ml of DMF. To the resulting mixture, a solution prepared by dissolving 6.7 g of p-trifluoromethylaniline in 10 ml DMF was dripped under stirring at room temperature, followed by stirring one hour. Then, the resultant mixture was heated at 150° C. for three hours with stirring. After cooling, a precipitated solid was filtered off. The precipitate was recrystallized from acetonitrile, followed by sublimation and purification, whereby 5.0 g of a pale pink solid of (I-1) was obtained.

As a result of an IR measurement of the compound obtained, absorption of a carbonyl group at 1710 cm$^{-1}$ was determined. Mass spectrometry revealed that the compound had a peak at an M/Z of 554.

This compound was dissolved in DMF to prepare 0.01 mol/l of a DMF solution. The DMF solution was measured for reduction potential by cyclic voltammetry in the same manner as in Example 1, and was found to be −0.33 V.

Example 3

Synthesis of (I-5)

The same procedures as in Example 1 were followed, except that 6.0 g of 3,4,5-trifluoroaniline was used instead of p-trifluoromethylaniline of example 2, whereby 4.3 g of a pale yellow solid of (I-5) was obtained.

As a result of an IR measurement of the compound obtained, absorption of a carbonyl group at 1710 cm$^{-1}$ was determined. Mass spectrometry revealed that the compound had a peak at an M/Z of 526.

The reduction potential of the compound was measured by cyclic voltammetry in the same manner as in Example 2, and was found to be −0.33 V.

Example 4

Synthesis of (I-6)

4.6 g of naphthalene tetracarboxylic anhydride was added to 45 ml of DMF. To the resulting mixture, a solution prepared by dissolving 5.2 g of 4-amino-1,2-phthalonitrile in 10 ml DMF was dripped under stirring at room temperature, followed by stirring for one hour. Then, the resultant mixture was heated at 150° C. for three hours with stirring. After cooling, 50 ml of methanol was added, and then a precipitated solid was filtered off. The precipitate was recrystallized from acetonitrile, followed by sublimation and purification, whereby 3.7 g of a pale yellow solid of (I-6) was obtained.

As a result of an IR measurement of the compound obtained, absorption of a carbonyl group at 1710 cm$^{-1}$ was determined. Mass spectrometry revealed that the compound had a peak at an M/Z of 518.

The reduction potential of the compound was measured by cyclic voltammetry in the same manner as in Example 2, and was found to be −0.30 V.

Example 5

Synthesis of (II-6)

3.7 g of pyromelletic anhydride and 5.2 g of 4-amino-1,2-phthalonitrile were added to 45 ml of DMF. Thereafter, the same procedures as in Example 4 were followed, whereby 3.1 g of a pale yellow solid of (II-6) was obtained.

As a result of an IR measurement of the compound obtained, absorption of a carbonyl group at 1715 cm$^{-1}$ was determined. Mass spectrometry revealed that the compound had a peak at an M/Z of 468.

The reduction potential of the compound was measured by cyclic voltammetry in the same manner as in Example 2, and was found to be −0.32 V.

[Organic EL Device]

Example 6

A 25 mm×75 mm glass substrate with a thickness of 1.1 mm provided with transparent electrodes formed of ITO (manufactured by Geomatics Corporation) was subjected to ultrasonic cleaning for five minutes in isopropyl alcohol, followed by UV/ozone cleaning for 30 minutes.

The cleaned glass substrate having the transparent electrode lines was then secured to a substrate holder of an apparatus for vacuum deposition. First, the compound represented by the formula (A-1) synthesized in Example 1 and the compound represented by the following formula (C-1) were deposited onto the surface of the glass substrate on which the transparent electrode lines are formed so as to cover the transparent electrodes, thereby forming a 60 nm-thick film in which the compound of the formula (A-5) and the compound of the formula (C-1) were mixed at a molar ratio of 2:98. The film of the compound mixture served as a hole injecting layer.

Subsequently, a 20 nm-thick film of a compound represented by the following formula (HTM-1) was formed on the above-obtained film of the compound mixture. The film served as a hole transporting layer.

Further, a compound represented by the following formula (EM1) with a thickness of 40 nm was deposited thereon to form a film. Simultaneously, an amine compound (D1) having the following styryl group as an emitting molecule was deposited such that the weight ratio of EM1 and D1 was 40:2. The film served as an emitting layer.

A compound (Alq) represented by the following formula was deposited to form a 10 nm thick film on the above-obtained film. The film serves as an electron injecting layer. Then, Li as a reductive dopant (Li source: manufactured by SAES Getters Co., Ltd.) and Alq were co-deposited, whereby an Alq:Li film (film thickness: 10 nm) was formed as an electron injecting layer (cathode). Metal aluminum was deposited on the Alq:Li film to form a metallic cathode, whereby an organic EL emitting device was fabricated.

The organic EL device was evaluated by measuring a driving voltage at a current density of 10 mA/cm$^2$ and a half life of luminance at an initial luminance of 1,000 nits, at room temperature, and with a DC constant power supply. The results obtained are shown in Table 1.

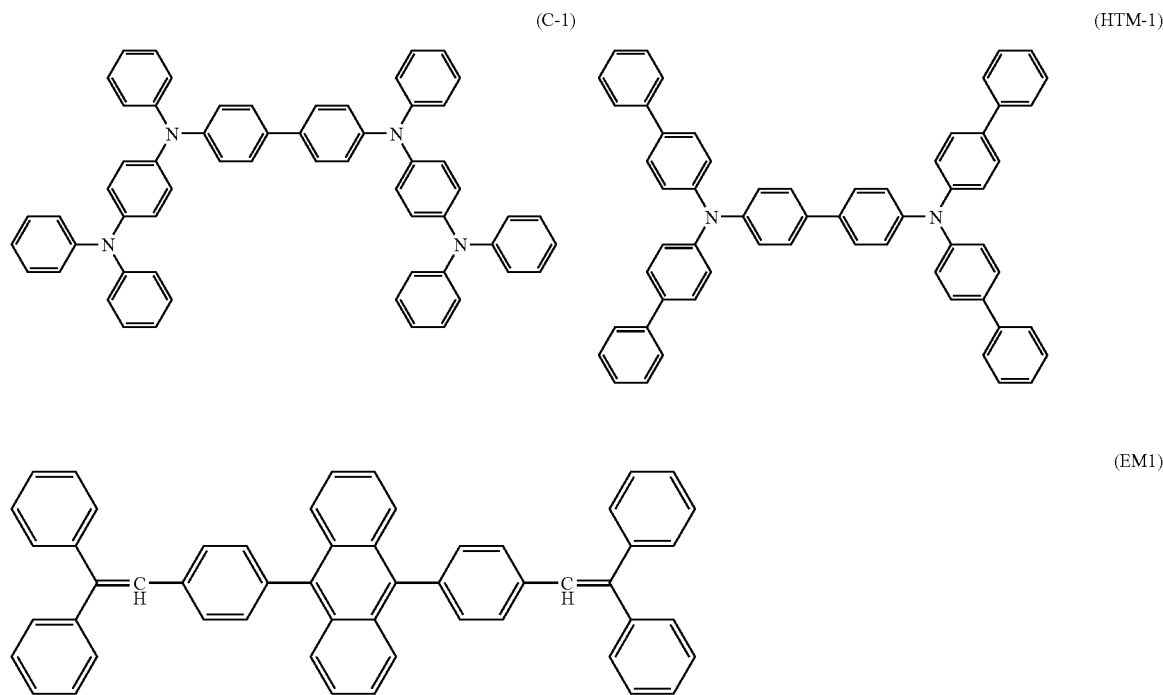

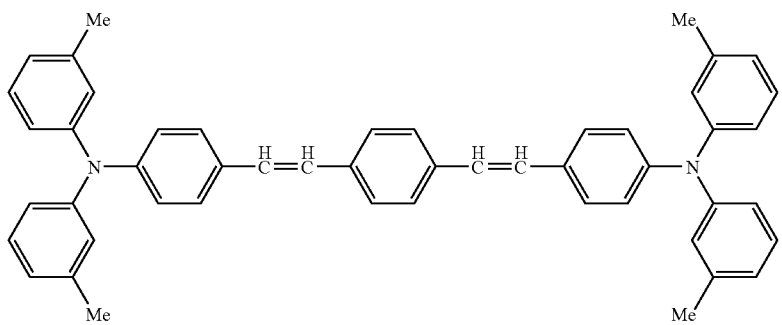

D1

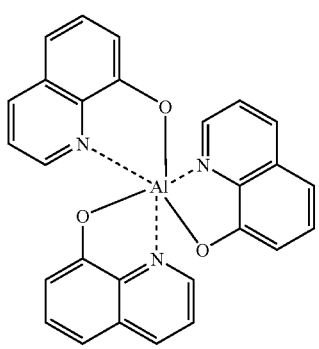

Alq

Example 7

An organic EL device was fabricated and evaluated in the same manner as in Example 6, except that the hole injecting layer was formed using the compound represented by the formula (I-6) synthesized in Example 4 instead of the compound represented by the formula (A-1).

The results obtained are shown in Table 1.

Comparative Example 1

An organic EL device was fabricated and evaluated in the same manner as in Example 6, except that the hole injecting layer was formed using the compound represented by the formula (C-1) singly.

The results obtained are shown in Table 1.

TABLE 1

|  | Constitution materials for hole-injecting layer | Driving voltage (V) | Half life (hr) |
| --- | --- | --- | --- |
| Example 6 | Compounds of formulas (A-1) and (C-1) | 5.7 | 6,600 |
| Example 7 | Compounds of formulas (I-6) and (C-1) | 6.0 | 6,800 |
| Comparative Example 1 | Compound of formula (C-1) | 6.6 | 5,600 |

INDUSTRIAL APPLICABILITY

The imide derivative or the material for an organic EL device of the invention is suitable as a constitution material of an organic EL device, in particular, a hole transporting layer or a hole injecting layer. The material for an organic EL device of the invention can also be used as a charge-transporting material of an electrophotographic photoreceptor. Furthermore, the imide derivative or the material for an organic EL device of the invention is also suitable as an organic photoreceptor and a material for an organic solar cell.

The organic EL device of the invention can be suitably used as a light source such as a planar emitting material and backlight of a display, a display part of a portable phone, PDA, a car navigator, or an instruction panel of an automobile, an illuminator, and the like.

What is claimed is:

1. A material represented by the following formula (II):

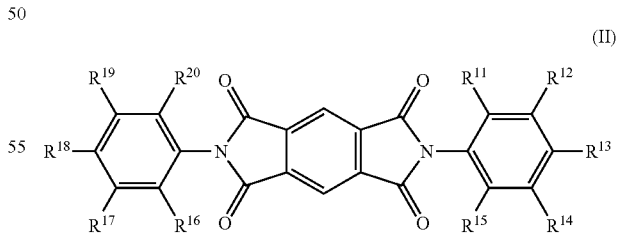

(II)

wherein $R^{11}$ to $R^{20}$ are each a hydrogen atom, a fluorine atom, a fluoroalkyl group or a cyano group, provided that a material wherein all of $R^{11}$ to $R^{20}$ are a hydrogen atom is excluded.

2. A material according to claim 1 which has a reduction potential (vs saturated calomel electrode) in a dimethylformamide solution of −0.5 V or more.

3. An organic electroluminescent device comprising:
an anode,
a cathode, and
one or a plurality of organic thin layers, including an emitting layer, the organic thin layers being interposed between the anode and the cathode;
at least one of the organic thin layers comprising the material of claim 1.

4. The organic electroluminescent device according to claim 3 wherein the organic thin layers are a multilayer body in which a hole transporting layer, an emitting layer and an electron transporting layer are stacked in this order from the anode.

5. The organic electroluminescent device according to claim 4 wherein the hole transporting layer comprises the material.

6. The organic electroluminescent device according to claim 3 wherein the organic thin layers are a multilayer body in which a hole injecting layer, a hole transporting layer, an emitting layer, and an electron transporting layer are stacked in this order from the anode; the hole injection layer comprising the material.

7. The organic electroluminescent device according to claim 5 wherein the hole transporting layer comprising the material further comprises a phenylenediamine compound represented by the following formula (III):

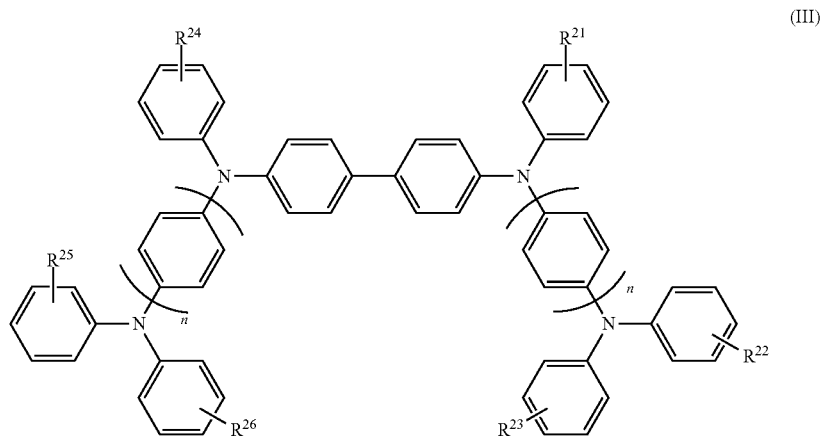

wherein $R^{21}$ to $R^{26}$ are a hydrogen atom, a halogen atom, a trifluoromethyl group, an alkyl group, an aryl group, or a heterocycle; $R^{21}$ to $R^{26}$ may form a naphthalene skeleton, a carbazole skeleton, or a fluorene skeleton with a phenyl group bonded; and n represents 1 or 2.

8. The organic electroluminescent device according to claim 6 wherein the hole injecting layer comprising the material further comprises a phenylenediamine compound represented by the following formula (III):

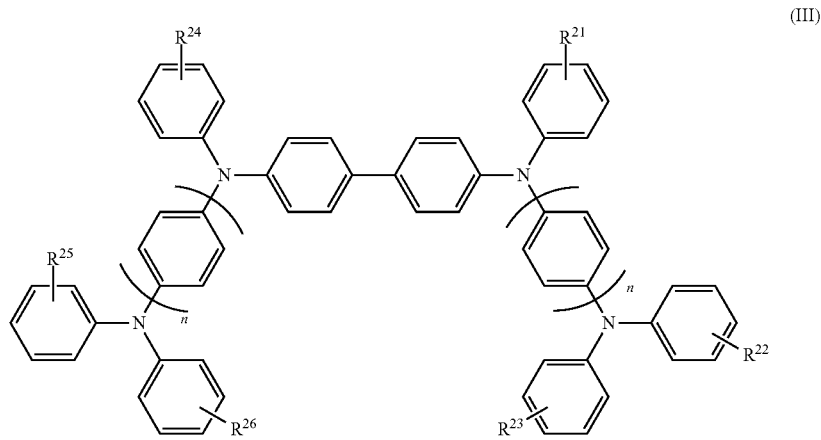

wherein $R^{21}$ to $R^{26}$ are a hydrogen atom, a halogen atom, a trifluoromethyl group, an alkyl group, an aryl group, or a heterocycle; $R^{21}$ to $R^{26}$ may form a naphthalene skeleton, a carbazole skeleton, or a fluorene skeleton with a phenyl group bonded; and n represents 1 or 2.

9. A material according to claim 1, which has the following formulae (II-8) or (II-9):
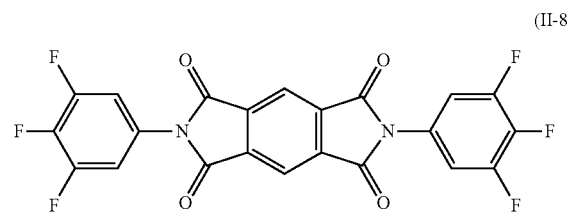
(II-8)
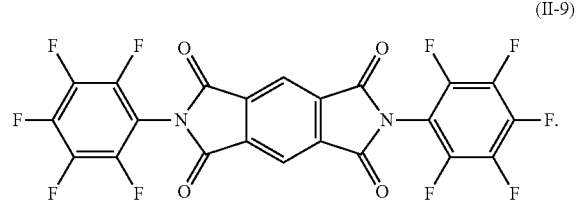
(II-9)
* * * * *